US007405825B2

(12) United States Patent
Schuurmans et al.

(10) Patent No.: US 7,405,825 B2
(45) Date of Patent: Jul. 29, 2008

(54) OPTICAL ANALYSIS SYSTEM

(75) Inventors: Frank Jeroen Pieter Schuurmans, Eindhoven (NL); Michael Cornelis Van Beek, Eindhoven (NL); Levinus Pieter Bakker, Eindhoven (NL); Wouter Harry Jacinth Rensen, Eindhoven (NL); Bernardus Hendrikus Wilhelmus Hendriks, Eindhoven (NL); Robert Frans Maria Hendriks, Eindhoven (NL); Thomas Steffen, Eindhoven (NL)

(73) Assignee: Koninklijke Philiips Electronics N. V., Eindhoven (NL)

( * ) Notice: Subject to any disclaimer, the term of this patent is extended or adjusted under 35 U.S.C. 154(b) by 181 days.

(21) Appl. No.: 10/539,540

(22) PCT Filed: Dec. 19, 2003

(86) PCT No.: PCT/IB03/06089

§ 371 (c)(1), (2), (4) Date: Oct. 27, 2005

(87) PCT Pub. No.: WO2004/057285

PCT Pub. Date: Jul. 8, 2004

(65) Prior Publication Data
US 2006/0158734 A1    Jul. 20, 2006

(30) Foreign Application Priority Data
Dec. 19, 2002  (EP) ................................. 02080427

(51) Int. Cl.
G01J 3/32 (2006.01)
G01J 3/457 (2006.01)
G02B 26/02 (2006.01)

(52) U.S. Cl. ........................ 356/326; 359/297; 356/330

(58) Field of Classification Search ................. 356/326; 359/290, 291, 295, 296, 297
See application file for complete search history.

(56) References Cited

U.S. PATENT DOCUMENTS 4,701,021 A * 10/1987 Le Pesant et al. ........... 359/228
4,790,654 A * 12/1988 Clarke ........................ 356/310
5,090,807 A *  2/1992 Tai ............................. 356/310

(Continued)

FOREIGN PATENT DOCUMENTS

EP           1 318 426  A1      6/2003

(Continued)

OTHER PUBLICATIONS

Alt, P.M.; Single Crystal Silicon for High Resolution Displays; 1997; Proc. 17th Int. Display Res. Conf., pp. M-19-28.

(Continued)

*Primary Examiner*—Gregory J. Toatley, Jr.
*Assistant Examiner*—Bryan Giglio

(57) ABSTRACT

The optical analysis system (20) for determining an amplitude of a principal component of an optical signal comprises a multivariate optical element (10) for reflecting the optical signal and thereby weighing the optical signal by a spectral weighing function, and a detector (9, 9P, 9N) for detecting the weighed optical signal. The optical analysis system (20) may further comprise a dispersive element (2) for spectrally dispersing the optical signal, the multivariate optical element being arranged to receive the dispersed optical signal. The blood analysis system (40) comprises the optical analysis system (20) according to the invention.

16 Claims, 13 Drawing Sheets

U.S. PATENT DOCUMENTS

| | | | |
|---|---|---|---|
| 5,486,485 A | | 1/1996 | Kim et al. |
| 5,504,575 A | | 4/1996 | Stafford |
| 5,737,076 A | | 4/1998 | Glaus et al. |
| 5,748,308 A | * | 5/1998 | Lindberg et al. ............ 356/310 |
| 6,128,078 A | * | 10/2000 | Fateley ....................... 356/330 |
| 6,198,531 B1 | | 3/2001 | Myrick et al. |
| 6,504,943 B1 | * | 1/2003 | Sweatt et al. ............... 382/103 |
| 6,859,275 B2 | * | 2/2005 | Fateley et al. ............... 356/330 |
| 6,967,763 B2 | * | 11/2005 | Fujii et al. .................. 359/297 |
| 7,123,796 B2 | * | 10/2006 | Steckl et al. ................. 385/40 |
| 2002/0057431 A1 | * | 5/2002 | Fateley et al. ............... 356/330 |
| 2003/0161039 A1 | | 8/2003 | Fukano et al. |

FOREIGN PATENT DOCUMENTS

| | | |
|---|---|---|
| JP | 2000-356751 | 12/2000 |
| WO | WO 02/057759 A1 | 7/2002 |

OTHER PUBLICATIONS

Dudley, D., et al.; Emerging Digital Micromirror Device Applications; 2003; SPIE; 4985: 14-25.

Hayes, R.A., et al.; Video-speed electronic paper based on electrowetting; 2003; Nature; 25:383-385.

Sato, F., et al.; High Resolution and Bright LCD Projector with Reflective LCD Panels; 1997; SID Int'l Symposium; pp. 997-1000.

Shimizu, J.A.; Single panel reflective LCD projector; 1999; SPIE; 3634:197-206.

* cited by examiner

OPTICAL ANALYSIS SYSTEM

The invention relates to an optical analysis system for determining an amplitude of a principal component of an optical signal, the optical analysis system comprising a multivariate optical element (MOE) for weighing the optical signal by a spectral weighing function, and a detector for detecting the weighed optical signal.

The invention further relates to a blood analysis system comprising such an optical analysis system.

The invention further relates to a method of determining an amplitude of a principal component of an optical signal, the method comprising the steps of weighing the optical signal by a MOE having a spectral weighing function, and detecting the weighed optical signal by a detector.

U.S. Pat. No. B1-6,198,531 discloses an embodiment of an optical analysis system described in the opening paragraph.

The known optical analysis system is part of a spectroscopic analysis system suited for, e.g., analyzing which compounds are comprised at which concentrations in a sample. It is well known that light interacting with the sample carries away information about the compounds and their concentrations. The underlying physical processes are exploited in optical spectroscopic techniques in which light of a light source such as, e.g., a laser, a lamp or light emitting diode is directed to the sample for generating an optical signal which carries this information.

For example, light may be absorbed by the sample. Alternatively or in addition, light of a known wavelength may interact with the sample thereby generating light at a different wavelength due to, e.g., a Raman process. The transmitted and/or generated light then constitutes the optical signal which may also be referred to as the spectrum. The relative intensity of the optical signal as function of the wavelength is then indicative for the compounds comprised in the sample and their concentrations.

To identify the compounds comprised in the sample and to determine their concentrations the optical signal has to be analyzed. In the known optical analysis system the optical signal is analyzed by dedicated hardware comprising an optical filter. This optical filter has a transmission which depends on the wavelength, i.e. it is designed to weigh the optical signal by a spectral weighing function which is given by the wavelength dependent transmission. The spectral weighing function is chosen such that the total intensity of the weighed optical signal, i.e. of the light transmitted by the filter, is directly proportional to the concentration of a particular compound. Such an optical filter is also referred to as a MOE. This intensity may be conveniently detected by a detector such as, e.g., a photo diode. For every compound a dedicated optical filter with a characteristic spectral weighing function is used. The optical filter may be, e.g., an interference filter having a transmission constituting the desired spectral weighing function.

For a successful implementation of this analysis scheme it is essential to know the spectral weighing functions corresponding to the compounds of interest. The spectral weighing function may be obtained by performing a principal component analysis of a set comprising N or more spectra of N pure compounds of known concentration where N is an integer. Each spectrum comprises the intensity of the corresponding optical signal at M different wavelengths where M is an integer as well. Typically, M is much larger than N. Each spectrum containing M intensities at corresponding M wavelengths constitutes a M dimensional vector whose M components are these intensities. These vectors are subjected to a linear-algebraic process known as singular value decomposition (SVD) which is at the heart of principal component analysis and which is well understood in this art.

As a result of the SVD a set of N eigenvectors $z_n$ with n being a positive integer smaller than N+1 is obtained. The eigenvectors $z_n$ are linear combinations of the original N spectra and often referred to as principal component vectors or regression vectors. Typically, the principal component vectors are mutually orthogonal and determined as normalized vectors with $|z_n|=1$. Using the principal component vectors $z_n$, the optical signal of a sample comprising the compounds of unknown concentration may be described by the combination of the normalized principal component vectors multiplied by the appropriate scalar multipliers:

$$x_1 z_1 + x_2 z_2 + \ldots + x_n z_n,$$

The scalar multipliers $x_n$ with n being a positive integer smaller than N+1 may be considered the amplitudes of the principal component vectors Z, in a given optical signal. Each multiplier $x_n$ can be determined by treating the optical signal as a vector in the M dimensional wavelength space and calculating the direct product of this vector with a principal component vector $z_n$. The result yields the amplitude $x_n$ of the optical signal in the direction of the normalized eigenvector $z_n$. The amplitudes $x_n$ correspond to the concentrations of the N compounds.

In the known optical analysis system the calculation of the direct product between the vector representing the optical signal and the principal component vector is implemented in the hardware of the optical analysis system by means of the optical filter. The optical filter has a transmittance such that it weighs the optical signal according to the components of the principal component vector, i.e. the principal component vector constitutes the spectral weighing function. The filtered optical signal may be detected by a detector which generates a signal with an amplitude proportional to the amplitude of the principal component vector and thus to the concentration of the corresponding compound.

In a physical sense, each principal component vector is a constructed "spectrum" with a shape in a wavelength range within the optical signal. In contrast to a real spectrum, a principal component vector may comprise a positive part in a first spectral range and a negative part in a second spectral range. In this case the principal component vector has positive components for the wavelengths corresponding to the first spectral range and negative components for the wavelengths corresponding to the second spectral range.

It is a disadvantage of the known optical analysis system that it requires a relatively large amount of space. This is particularly disadvantageous when the optical analysis system is used for applications where little space is available, e.g. in space, in an emergency room of a hospital or in a portable device.

It is an object of the invention to provide an optical analysis system of the kind described in the opening paragraph, which may be realized in a relatively small space.

According to the invention the object is realized in that the MOE reflects the optical signal and thereby weighs the optical signal by the spectral weighing function. Because the MOE is operated in reflection and not in transmission as in the known optical analysis system, it may be realized in a more compact space.

According to the invention the optical signal is not restricted to optical signals having wavelengths which are visible by the human eye. The optical signal may comprise spectral components in the ultra violet (UV) and/or in the infra red (IR) spectral. Here, the IR spectral range may comprise the near infra red (NIR) and the far infra red (FIR) which has a frequency above 1 THz, and all intermediate wavelengths as well.

According to the invention the principal component is not limited to a pure principal component. Here, a pure principal component refers to a mathematically exact eigenvector for a certain compound. A principal component may also comprise minor contributions from other compounds which may result from imperfections during determining the principal components. A principal component may also correspond to a mixture of several compounds of known concentrations. A principal component may correlate with one or more particular analytes where the term "correlate" may include substantially complete correlation or partial correlation. The principal component may not correlate with analytes other than these one or more particular analytes where the term "not correlate" may include substantially no correlation or partial correlation, provided that this latter partial correlation is smaller than the partial correlation with the with one or more particular analytes. The spectral weighing function and/or the principal component may also be called a regression vector.

The spectral weighing function may be obtained by the principal component analysis or by any other mathematical orthogonalisation procedure, any multivariate analysis method, for example partial least squares (PLS), a generic algorithm or a neural network.

The principal component may relate to an electronic, vibrational and/or vibronic transition of an analyte. The further component may relate to an electronic, vibrational and/or vibronic transition of a substance other than the analyte. The principal component may relate to a Raman spectrum of an analyte. The further component may relate to a fluorescence spectrum of a substance carrying the analyte and/or of the analyte itself or to a fluorescence spectrum of a substance in between the detection volume and the detector such as human skin tissue or optical elements.

The MOE may have a spectral weighing function which is adjustable.

In an embodiment the optical analysis system further comprises a dispersive element such as, e.g., a grating or a prism for spectrally dispersing the optical signal, the MOE being arranged to receive the dispersed optical signal. In such an optical analysis system-different regions of the MOE receive different spectral portions of the optical signal. For instance one region may receive e.g. the blue spectral portion and another region may receive the red spectral portion. A spectral portion may be defined as a range of wavelengths.

The reflectivity of these regions may be adjusted per region to obtain the spectral weighing function. This may be more accurate and less complicated than designing the spectral reflectance of the MOE known in the prior art which is an interference filter. In the known MOE all spectral portions are incident on the same region of the MOE. It is then relatively complicated and difficult to obtain the required reflectance for all spectral portions.

The MOE may comprise a region for receiving a spectral portion of the dispersed optical signal, the region having a reflectivity relating to the spectral weighing function. The reflectivity of the entire region may be adjusted such that the spectral component incident on this region is weighed according to the spectral weighing function. Different regions corresponding to different spectral components may have different reflectivities according to the spectral weighing function. The reflectivity of the entire region may be constant which allows for a relatively simple way to adjust it, e.g. by controlling the thickness of a reflective metal coating on a surface constituting the region. The reflectivity of the entire region or of only a part of the region-may be adjustable. The region may comprise a number of parts which each have an individually adjustable reflectivity. Embodiments of MOEs with an adjustable reflectivity are given below.

Alternatively or in addition the MOE may comprise a region for receiving a spectral portion of the dispersed optical signal, a part of the region being arranged to reflect the dispersed optical signal incident thereon to the detector, another part of the region being arranged to prevent the dispersed optical signal incident thereon from being reflected to the detector. In this case the region comprises two parts, one part reflects the spectral portion incident on this part to the detector, the other part prevents that the spectral portion incident on this latter part is reflected to the detector. The latter part may be absorbed or reflected elsewhere, e.g. to a beam dump. The latter part may be at least partly be detected by an additional detector, e.g. for calibration of the emission intensity or wavelength of a light source in a spectroscopic system. The relative intensity of the spectral portions incident on the respective parts and the reflectivity of the part reflected the optical signal to the detector determine the weighing of the optical signal in the respective spectral portion.

Such a MOE has the advantage of a relatively high contrast because only relatively small amounts of light incident on the part may not reach the detector whereas only relatively small amounts of light incident on the other part may still reach the detector. These unwanted processes are mainly determined by the optical quality of the reflecting surfaces. The quality of these surfaces may be well controlled at relatively low cost. Furthermore, the reflectivity is relatively insensitive to the polarization state of the light.

The word "arranged" may imply that the part and the other part may be arranged permanently e.g. by forming a structured reflective surface as shown in and described with reference to FIGS. 11A and 11B, but it is not restricted to this. It may also imply that the region comprises a tiltable reflective surface. Depending on the position of the tiltable reflective surface the spectral portion incident thereon may be reflected to the detector or may be reflected elsewhere such that it is not detected, e.g. to a beam dump. In this way the spectral weighing function may at least partly be adjusted by the position of the tiltable reflective surface. In one tilt position it may be oriented such that it reflects the spectral component incident thereon to the detector. In another tilt position it may be oriented such that it reflects the spectral component incident thereon away from the detector.

When the tiltable reflective surface is part of a relatively small tiltable element, the switching time of the tiltable surface, i.e. the time required to direct the reflected light to or away from the detector, may be relatively short The reflective surface may have a size of e.g. 10 micron by 10 micron, and may have a distance of 14 micron to the adjacent reflective surface, if present. The switching time may be in the order of 20 microseconds.

The region may comprise more than one tiltable surface each of which may be individually tiltable. In this way the relative amount of the spectral portion to be reflected to the detector may be adjusted by orienting a respective number of tiltable surfaces such that they reflect the spectral component incident thereon to the detector. The higher the number of tiltable surface the higher the accuracy with which the spectral weighing function may be adjusted.

The spectral weighing for a certain spectral portion of the optical signal may be executed by one cell. The cell may be switched between a position in which the spectral component incident thereon is reflected to the detector, and a further position in which the spectral component incident thereon is reflected elsewhere. The spectral weighing is then determined by the time the cell is in the position versus the further time in which it is in the further position. In other words, the amplitude of the spectral portion is determined by the duty cycle of the cell. The detector may comprise an integrator to integrate the signal over a certain time period which may be the time plus the further time.

The MOE may comprise two or more regions, each region being arranged to receive a respective spectral portion of the optical signal and each region comprising at least one tiltable reflective surface. In this way the spectral weighing function may be adjusted in the two respective wavelength ranges. The reflectivity may be relatively independent of the wavelength, as is known for e.g. metal, semiconducting and/or dielectric surfaces of single or multiple layers. The reflectivity of the region may then be adjusted relatively easily by adjusting the surface areas of the part and the other part. It is not required to account for the change of the reflectivity as function of the wavelength due to the achromaticity.

The MOE may comprise an array of individually tiltable reflecting surface. The tiltable reflecting surface may be part of a tiltable element. The tilt of each of the elements may be induced by applying an electrostatic potential difference between the element and an electrode facing the element. Such an array may be a digital mirror device (DMD) as described e.g. in the article "Emerging Digital Micromirror Device (DMD) Applications" by D. Dudley, W. M. Duncan, J. Slaughter, Proceedings of SPIE 4985, p. 14-25 (2003).

The region may comprise a reflective liquid crystal (LC) cell. Such a cell comprises a layer of LC molecules which may be at least partly be orientated by applying an electric field. The layer of at least partly oriented LC molecules has an anisotropic index of refraction such as an ordinary index of refraction along an ordinary axis and an extraordinary index of refraction along an extraordinary direction, where the ordinary index of refraction is different from the extraordinary index of refraction. When light with a polarization direction different to the ordinary direction or the extraordinary direction passes through this layer, the polarization state of the light is altered. In a reflective LC cell the layer of LC molecules is located in front of a reflective surface such that the light passed through the layer is reflected back to pass through the layer once more. Prior to passing the light through the layer of LC molecules the polarization state of the light may be adjusted by a polarizer. The change in the polarization state of light may be measured by passing the light after the dual pass through the layer of LC molecules through an analyzer. The polarizer may be used as the analyzer.

The amount of the spectral portion incident on the LC cell which is detected by the detector may be adjusted by adjusting the orientation of the LC molecules. In other words, the spectral weighing function may at least partly be adjusted by applying a voltage to the LC cell and thereby orienting the LC molecules.

Reflective LC cells are well known in the art as such and may be obtained for a relatively low price. They allow for an adjustable reflection without requiring moving parts. The orientation of LC molecules may be relatively slow such as in the order of several milliseconds.

The region may comprise more than one reflective LC cell each of which may be individually adjustable. The amount of the spectral component reflected to the detector may be adjusted by adjusting the voltage applied. Alternatively, the relative amount of the spectral portion to be reflected to the detector may be adjusted by providing a respective number of reflective LC cells with a voltage such that they reflect the spectral component incident thereon to the detector and the remainder of the cells with a voltage such that they substantially do not reflect the spectral component incident thereon to the detector. In such a scheme a digital rather than an analog voltage control may be used which reduces the costs of the electronics required. The higher the number of reflective LC cells the higher the accuracy with which the spectral weighing function may be adjusted.

The MOE may comprise two or more regions, each region being arranged to receive a respective spectral portion of the optical signal and each region comprising at least one reflective LC cell. In this way the spectral weighing function may be adjusted in the two respective wavelength ranges. For LC molecules the anisotropic index of refraction may depend relatively strongly on the wavelength of the light. This effect is to be accounted for when adjusting the voltage which may complicate the control of such a MOE.

The MOE may comprise an array of individually controllable reflective LC cells. The LC cell may be a LC on silicon (LCoS) cell. The MOE may comprise an array of LCoS cells as described e.g. in U.S. Pat. No. 5,486,485, and in the articles "High resolution and bright LCD projector with reflective LCD panels" by F. Sato, Y. Yagi, K Hanihara, SID International Symposium, Boston (USA) (1997), Digest of Technical Papers XXVIII 997, "Single crystal silicon for high resolution displays" by P. M. Alt, Proceedings of the 17th International Display Research Conference, Toronto (Canada) (1997) M-19 and "Single panel reflective LCD projector" by J. A. Shimizu, Proceedings of SPIE 3634 (1999) 197.

The region may comprise a reflective electro-wetting cell. Such a cell comprises an absorbing liquid which is arranged to absorb the incident light. The absorbing liquid is comprised in a cell which comprises a surface which may be wetted by the absorbing liquid. It further comprises an electrode for applying a voltage between the electrode and the absorbing liquid. By applying such a voltage the wetting properties of the surface may be altered. In this way the absorbing liquid may be moved such that it substantially covers the surface or such that the reflecting surface is substantially free from the absorbing liquid. The cell further comprises a reflective surface which may be the surface being wetted by the absorbing liquid or which may be situated downstream this surface in the path of the incident light. When the reflecting surface is substantially free from the absorbing liquid the light is reflected whereas it is absorbed when the reflecting surface is substantially covered by the absorbing liquid. In other words, the spectral weighing function may at least partly be adjusted by applying a voltage to the electro-wetting cell and thereby positioning the absorbing liquid.

Reflective electro-wetting cells are well known in the art per se, see e.g. the article "Video-speed electronic paper based on electro-wetting" by R. A. Hayes and B. J. Feenstra, Nature 425, p. 383-385 (2003). They allow for an adjustable reflection without requiring moving parts. The movement of the absorbing liquid may be faster than the orientation of the LC molecules.

The region may comprise more than one reflective electro-wetting cell each of which may be individually adjustable. The amount of the spectral component reflected to the detector may be adjusted by adjusting the voltage applied. Alternatively, the relative amount of the spectral portion to be reflected to the detector may be adjusted by providing a respective number of reflective electro-wetting cells with a voltage such that they reflect the spectral component incident thereon to the detector and the remainder of the cells with a voltage such that they substantially do not reflect the spectral component incident thereon to the detector. In such a scheme a digital rather than an analog voltage control may be used which reduces the costs of the electronics required. When the cell is not switched during the spectral analysis the following holds: the higher the number of reflective electro-wetting cells illuminated in a certain spectral range, the higher the accuracy with which the spectral weighing function may be adjusted in this spectral range. When the cell is switched during the spectral analysis, the amplitude of the reflected spectral portion of the optical signal may be determined by the duty cycle. The accuracy is then determined by the accuracy with which the cell may be switched.

The MOE may comprise two or more regions, each region being arranged to receive a respective spectral portion of the optical signal and each region comprising at least one reflective electro-wetting cell. In this way the spectral weighing function may be adjusted in the two respective wavelength ranges. For absorbing liquids known in the art of electro-wetting cells as such the absorption may depend relatively weakly on the wavelength of the light. The reflectivity of the region may then be adjusted relatively easily by adjusting the surface areas of the part and the other part. It is not required to account for the change of the reflectivity as function of the wavelength due to this achromaticity.

The MOE may comprise an array of individually controllable reflective electro-wetting cells as described e.g. in the article "Video-speed electronic paper based on electro-wetting" by R. A. Hayes and B. J. Feenstra, Nature 425, p. 383-385 (2003).

In an embodiment the optical analysis system has a first detector for detecting the optical signal weighted by a first spectral weighing function and a second detector for detecting the optical signal weighted by a second spectral weighing function, the MOE being arranged to reflect a first part of the dispersed optical signal weighted by the first spectral weighing function to the first detector and a second part of the optical signal weighted by the second spectral weighing function to the second detector.

According to this aspect of the invention the optical analysis system further comprises a dispersive element for spectrally dispersing the optical signal, and a distribution element for receiving the spectrally dispersed optical signal and for distributing a first part of the optical signal weighted by the first spectral weighing function to the first detector and a second part of the optical signal weighted by the second spectral weighing function to the second detector. The distribution element may be a reflective MOE.

This aspect of the invention has a particular advantage with respect to the known optical analysis system. In the known optical analysis system a part of the optical signal is directed to a first filter which weighs the optical signal by a first spectral weighing function, and a further part of the optical signal is directed a second filter which weighs the optical signal by a second spectral weighing function. The signal to noise ratio is relatively low in the known optical analysis system because a significant part of the optical signal is not detected by any of the detectors, but blocked by, e.g., the first optical filter or by the second optical filter. For instance, the optical signal received by the first optical filter comprises all information but the first filter transmits only that part of the optical signal corresponding to the first weighing function whereas the part of the optical signal corresponding to the second weighing function is blocked by the filter. The light blocked by the first optical filter and by the second optical filter is not detected which reduces the signal to noise ratio.

According to this aspect of the invention this reduction of the signal to noise ratio is at least partly avoided. To this end the optical analysis system comprises a dispersive element such as, e.g., a grating or a prism for spectrally dispersing the optical signal. The spectrally dispersed optical signal is received by a distribution element, i.e. different parts of the distribution element receive different wavelengths of the optical signal. For individual wavelengths the distribution element is arranged to distribute a first part of the optical signal weighted according to the first spectral weighing function to the first detector and a second part of the optical signal weighted according to the second spectral weighing function to the second detector. Thus instead of partly blocking the optical signal as is done by the first optical filter and the second optical filter of the known optical analysis system, the different parts of the optical signal are directed to different detectors. As a consequence a larger amount of the optical signal is detected, yielding an improved signal to noise ratio.

In an embodiment the principal component comprises a positive part in a first spectral range and a negative part in a second spectral range, the first part of the optical signal weighted by the first spectral weighing function corresponding to the positive part, the second part of the optical signal weighted by the second spectral weighing function corresponding to the negative part, the first detector and the second detector being coupled to a signal processor arranged to subtract a signal generated by the second detector from a signal generated by the first detector. In this embodiment an optical signal comprising a principal component having a positive part and a negative part may be analyzed with an improved signal to noise ratio. Typically, the first spectral range is free from the second spectral range.

In another embodiment the principal component comprises a first principal component and a second principal component, the first part of the optical signal weighted by the first spectral weighing function corresponding to the first principal component, the second part of the optical signal weighted by the second spectral weighing function corresponding to the second principal component. This optical analysis system is particularly suited for analyzing optical signals comprising two or more principal components. It provides the corresponding amplitudes of the two or more principal components with an improved signal to noise ratio.

In yet another embodiment the principal component comprises a first principal component and a second principal component, and the first principal component and/or the second principal component comprises a positive part in a first spectral range and a negative part in a second spectral range.

It is advantageous if the distribution element has a surface for receiving the spectrally dispersed optical signal, the surface comprising a first set of surface elements and a second set of surface elements, the surface elements of the first set being arranged to distribute the spectrally dispersed optical signal to the first detector, the surface elements of the second set being arranged to distribute the spectrally dispersed optical signal to the second detector. In this embodiment, each surface element receives depending on its position and its surface area a certain portion of the spectrally dispersed optical signal. The first weighing function is then determined by the positions and the surface areas of the surface elements of the first set, and the second weighing function is determined by the positions and the surface areas of the surface elements of the second set. The spectrally dispersed optical signal received by the surface may be reflected and/or diffracted by the surface. Alternatively, it may be transmitted and refracted and/or diffracted.

This embodiment has the advantage that the distribution element can be manufactured relatively easily by, e.g., using a transparent substrate such as e.g. glass substrate which is provided with surface elements by etching and/or polishing.

Alternatively, the substrate may be manufactured using an appropriately shaped mold. An additional advantage of a transparent substrate is that the loss of the optical signal is relatively low.

It is advantageous if the dispersive element is arranged to disperse the optical signal in a dispersive plane and the optical analysis system further comprises a focusing member for focusing the dispersed optical signal, the focusing member having a first focal distance in the dispersive plane and a second focal distance in a plane perpendicular to the dispersive plane, the first focal distance may be different from the second focal distance, the focusing member being arranged to focus the dispersed optical signal in the dispersive plane on the distribution element. In this embodiment the spectrally dispersed optical signal is focused on the distribution element such that the different spectral components of the optical signal are received by different, mutually well separated portions of the distribution element. It is then possible to selectively distribute different wavelengths to different detectors.

In this embodiment it is further advantageous if the optical analysis system further comprises a further focusing member for focusing the first part of the optical signal on the first detector. This allows one to use a first detector having a relatively small area for detection area for efficiently detecting the first part.

For an efficient detection using detectors with an even smaller detection area it is advantageous if the optical analysis system further comprises a further dispersive element for spectrally recombining the first part of the optical signal prior to focusing the first part on the first detector. The first part of the optical signal distributed by the distribution element is in principle still spectrally dispersed which limits the possibility to focus the first part to a small detection area. By using a further dispersive element, the first part of the optical signal is spectrally recombined which allows for focusing it to a smaller area Therefore, a smaller first detector placed in this focus can be used. Alternatively, a pin hole or aperture may be placed in this focus to implement a confocal detection scheme.

A MOE may comprise a first MOE weighing the optical signal by a first partial weighing function in series with a second MOE for weighing the optical signal weighed by the first partial weighing function by a second partial weighing function. By combining two separate MOEs in series the amplitude of the optical signal may be adjusted independent from distributing the weighed optical signal to the first detector and the second detector, respectively. For instance, the first MOE may adjust the amplitude of the optical signal in one or more spectral ranges, i.e. it may weigh the optical signal by a first partial weighing function. The second MOE may receive the optical signal weighed by the first partial weighing function and distribute it to the first detector and the second detector in a relative ratio determined by the second partial weighing function. The first spectral weighing function and the second spectral weighing function are then a product of the first partial weighing function and the respective part of the second partial weighing function. In this way the simultaneous weighing of an optical signal by a first spectral weighing function and by a second spectral weighing function may be achieved, even when using an adjustable MOE and/or when the first spectral weighing function and the second spectral weighing function partly overlap. It is then possible that in a particular spectral range the amplitudes of the optical signal weighed by the first spectral weighing function and of the optical signal weighed by the second spectral weighing function may be smaller than the amplitude of the entire optical signal.

Alternatively, the first MOE and the second MOE may be interchanged, i.e. the first MOE may distribute the optical signal towards the first detector and the second detector according to the first partial weighing function. Subsequently, the portions of the optical signal thus obtained may be weighed according to the second partial weighing function by the second MOE.

The MOE comprising two MOEs in series is efficient and has a high signal-to-noise ratio which increases the sensitivity and decreases the time required to determine the amplitude of the principal component. This advantage may be obtained in particular when the optical analysis system has two detectors for detecting the optical signal weighed by a first spectral weighing function and by a second spectral weighing function, respectively. The advantage is obtained for reflective MOEs according to the invention, but not restricted to this type of MOEs. It is also obtained for other MOEs which may be operated in transmission rather than in reflection. The first MOE and the second MOE may have different working principles such as one being reflective, the other being transmissive, they may have different dynamic ranges and/or different spectral resolutions. The first partial weighing function and/or the second partial weighing function may be fixed or adjustable. Different parts of a single device may be used as first MOE and as second MOE.

The optical analysis system may further comprise a light source for providing light for illuminating a sample comprising a substance having a concentration and thereby generating the principal component. The amplitude of the principal component may then relate to the concentration of the substance. The relation may be a linear relation between the amplitude and the concentration. Such an optical analysis system may be a spectroscopic analysis system.

The optical analysis system according to the invention may be part of a blood analysis system arranged to analyze a sample comprising blood. The sample may be in-vivo blood, i.e. still contained in a human or an animal, or in-vitro blood, i.e. blood extracted from a human or an animal. The analyte may comprise one or more elements selected from e.g. glucose, lactate, glycohemoglobin (HbA1c), hemoglobin, hematocrit, cholesterol (total, HDL, LDL), triglycerides, urea, albumin, creatinin, oxygenation, pH, bicarbonate, and many others. The principal component may comprise the Raman spectrum of the one or more elements. The further component may comprise the fluorescence spectrum of the medium in which the one or more elements are dissolved or contained. The medium may comprise water, human or animal skin tissue, optical elements in the light path, and/or immersion medium.

These and other aspects of the optical analysis system, the blood analysis system and the method of analyzing an optical signal according to the invention will be further elucidated and described with reference to the drawings, in which.

Figure 1:
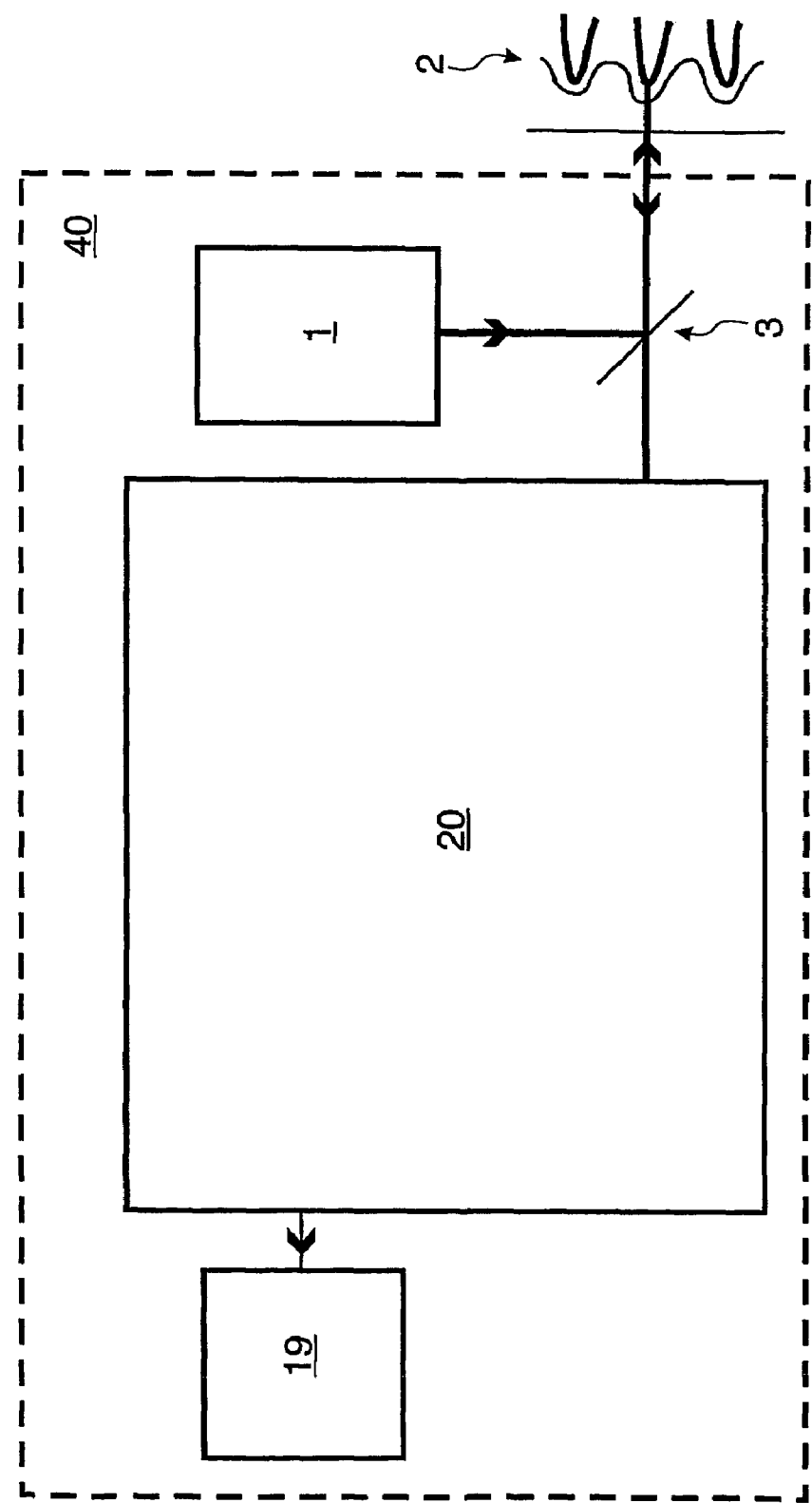
FIG. 1 is a schematic diagram of an embodiment of the blood analysis system.

In the embodiment shown in FIG. 1 the optical analysis system 20 for determining an amplitude of a principal component of an optical signal comprises a light source 1 for providing light for illuminating a sample 2 comprising a substance having a concentration and thereby generating the principal component. The amplitude of the principal component relates to the concentration of the substance. The light source 1 is a laser such as a gas laser, a dye laser and/or a solid state laser such as a semiconductor or diode laser.

The optical analysis system 20 is part of a blood analysis system 40. The sample 2 comprises skin with blood vessels. The substance may be one or more of the following analytes: glucose, lactate, cholesterol, oxy-hemoglobin and/or desoxy-hemoglobin, glycohemoglobin (HbAlc), hematocrit, cholesterol (total, HDL, LDL), triglycerides, urea, albumin, creatinin, oxygenation, pH, bicarbonate and many others. The concentrations of these substances is to be determined in a non-invasive way using optical spectroscopy. To this end the light provided by the light source 1 is sent to a dichroic mirror 3 which reflects the light provided by the light source towards the blood vessels in the skin. The light may be focused on the blood vessel using an objective 12. The light may be focused in the blood vessel by using an imaging and analysis system as described in the international patent application WO 02/057759.

By interaction of the light provided by the light source 1 with the blood in the blood vessel an optical signal is generated due to Raman scattering and fluorescence. The optical signal thus generated may be collected by the objective 12 and sent to the dichroic mirror 3. The optical signal has a different wavelength than the light provided by the light source 1. The dichroic mirror is constructed such that it transmits at least a portion of the optical signal.

Figure 2A:
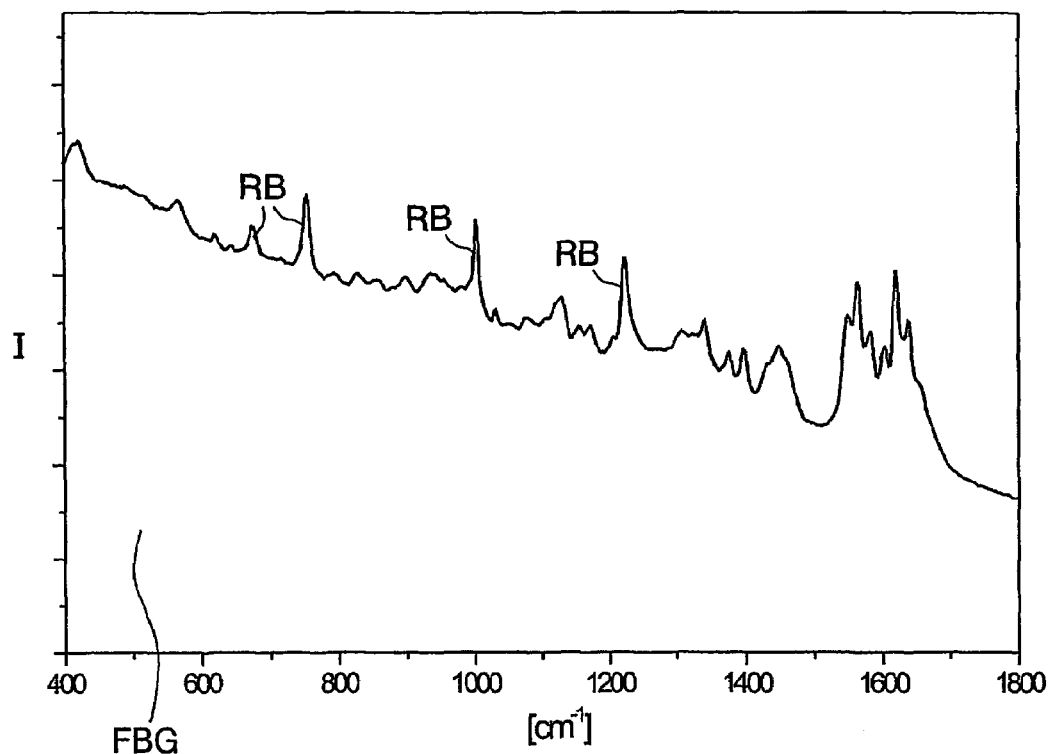
FIGS. 2A and 2B are spectra of the optical signal generated from blood in the skin and from a sample comprising one analyte in a solution.
Figure 2B:
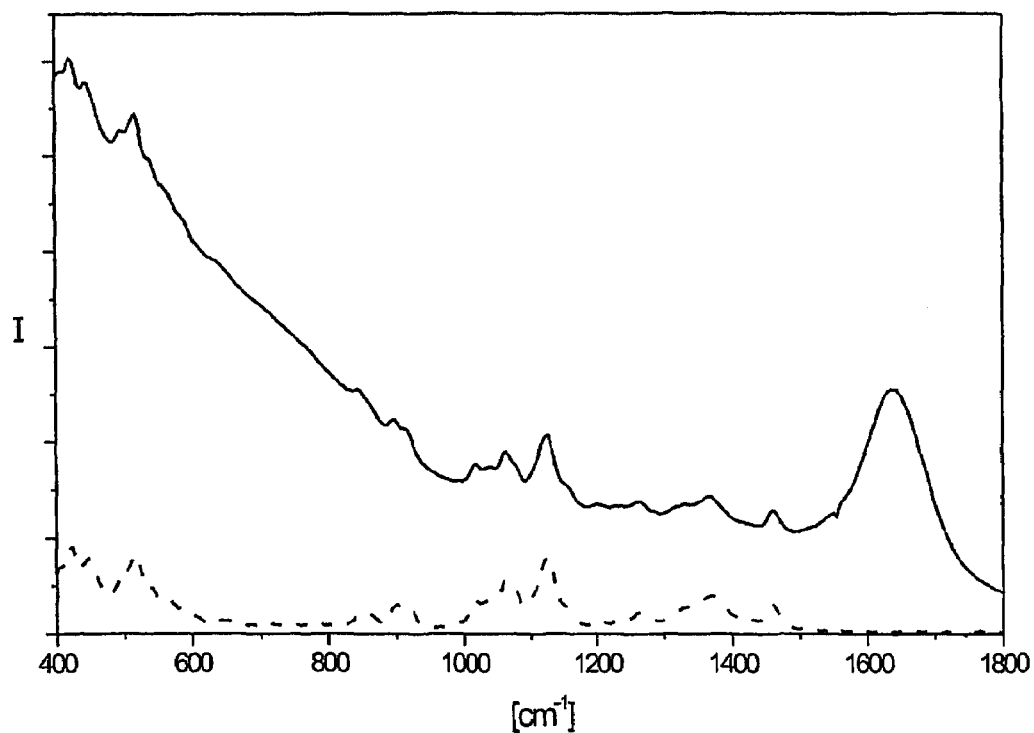

A spectrum of the optical signal generated in this way is shown in FIG. 2A. The spectrum comprises a relatively broad fluorescence background FBG and relatively narrow Raman bands RB. The x-axis of FIG. 2A denotes the wavelength shift with respect to the 785 nm of the excitation by light source 1 in wave numbers, the y-axis of FIG. 2A denotes the intensity in arbitrary units. The x-axis corresponds to zero intensity. The wavelength and the intensity of the Raman bands, i.e. the position and the height, is indicative for the type of analyte as is shown in the example of FIG. 2B for the analyte glucose which was dissolved in a concentration of 80 mMol in water. The solid line of FIG. 2B shows the spectrum of both glucose and water, the dashed line of FIG. 2B shows the difference between the spectrum of glucose in water and the spectrum of water without glucose. The amplitude of the spectrum with these bands is indicative for the concentration of the analyte.

Figure 3:
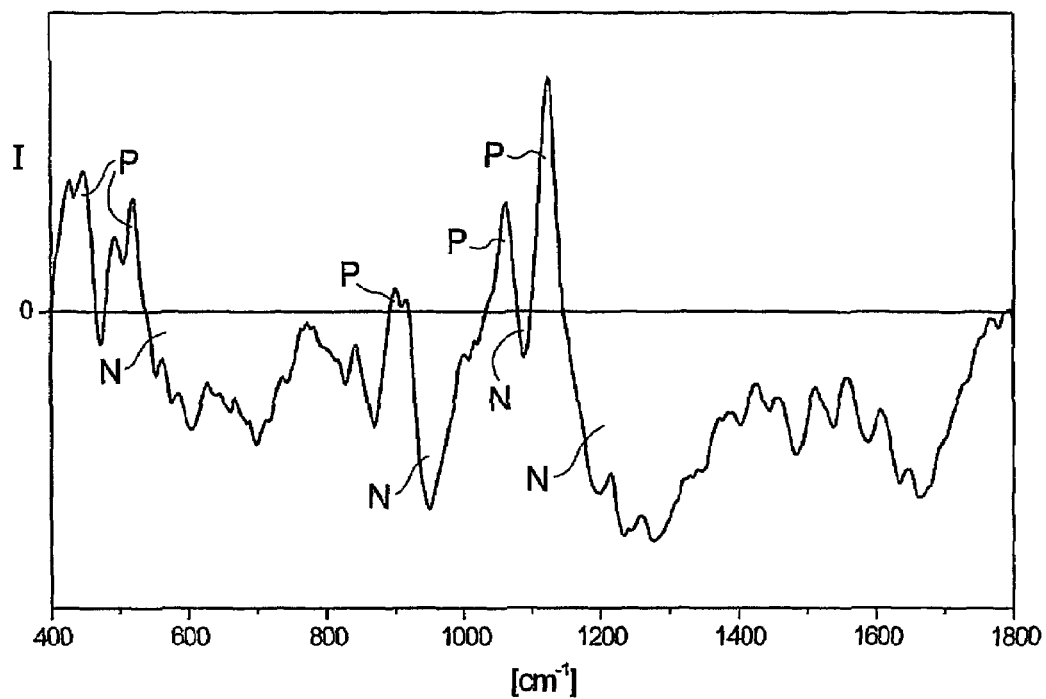
FIG. 3 is a spectral weighing function implemented in a MOE.

Because blood comprises many compounds each having a certain spectrum which may be as complex as that of FIG. 2B, the analysis of the spectrum of the optical signal is relatively complicated. The optical signal is sent to the optical analysis system 20 according to the invention where the optical signal is analyzed by a MOE which weighs the optical signal by a weighing function shown e.g. schematically in FIG. 3. The weighing function of FIG. 3 is designed for glucose in blood. It comprises a positive part P and a negative part N. The positive part P and the negative part N each comprise in this example more than one spectral band.

Figure 4:
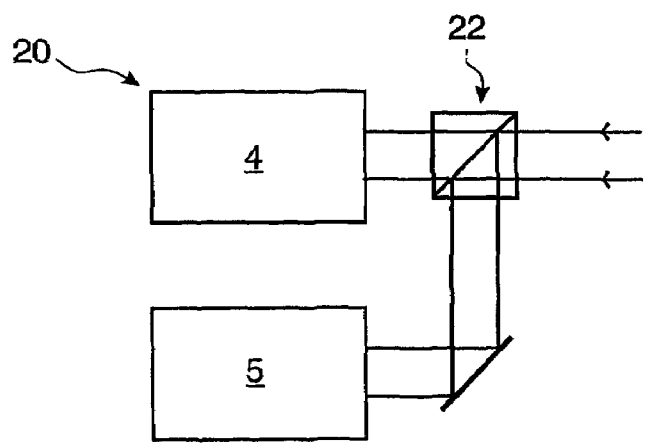
FIG. 4 is a schematic diagram of an embodiment of the optical analysis system.
Figure 5A:
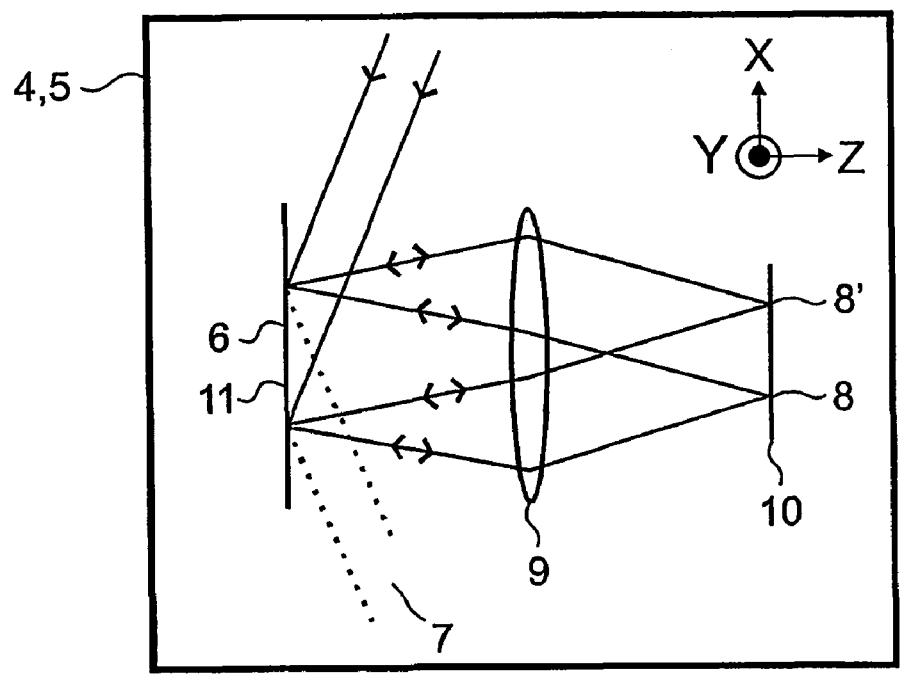
FIGS. 5A and 5B are schematic diagrams of the spectral filter of FIG. 4 in the x-z plane and the y-z plane, respectively.

In the embodiment of the optical analysis system 20 shown in FIG. 4 the light from the sample 2, i.e. the optical signal to be analyzed is split by a beam splitter 22 and s a to spectral filters 4, 5 shown in detail in FIG. 5A. The spectral filters 4, 5 are arranged to detect the optical signal weighed by the positive part and the negative part of the spectral weighing function, respectively. In the spectral filters 4, 5 the optical signal is directed to a dispersive element 6 which is a grating. The grating may partly reflect the optical signal specularly as is indicated by reference numeral 7. The dispersive element 6 at least partly diffracts the optical signal. Due to the diffraction the optical signal is spectrally dispersed and the different spectral components leave the grating under different angles. For illustration purposes this is depicted by rays 8 and 8' for two different wavelengths.

The dispersed optical signal is focused by a focusing member 9, which is a lens but may alternatively be a focusing mirror, onto the MOE 10 which is a DMD. It comprises an array of tiltable elements each having a tiltable reflective surface. The distance from the dispersive element 6 to the focusing member 9 equals the distance from the focusing member 9 to the MOE 10, which both correspond to the focal distance of the focusing member 9.

Here and in the remainder of this application the distance between a focusing member and another optical element is defined as the distance along the optical axis between the main plane of the focusing member and the main plane of the other optical element. When the focusing member has two main planes, as is the case e.g. for a thick lens, the main plane which is closest to the other optical element is to be used. When part of the space between the focusing member and the other optical element comprises a medium with an index of refraction different from 1, the optical distance, i.e. the geometric distance times the index of refraction is to be used.

The different spectral components portions of the dispersed optical signal are focused on different regions of the DMD along the x-direction as illustrated for two particular wavelengths by rays 8 and 8'. The DMD is oriented such that it reflects the optical signal out of the x-z plane either into the positive or the negative y-direction, i.e. each tiltable element of the DMD is tiltable around an axis parallel to the x-axis. A part of the region, i.e. a part of these elements is arranged to reflect the dispersed optical signal incident thereon to the detector 11. The corresponding tiltable reflective surfaces are oriented such that the respective reflections are directed to the detector 11. Another part of the region is arranged to prevent the dispersed optical signal incident thereon from being reflected to the detector 11. The corresponding tiltable reflective surfaces are oriented such that the respective reflections are directed to a beam dump. This is shown schematically in FIG. 5B. The reflections are focused again by the focusing member 9 and subsequently the optical signal reflected by the elements is detected by the detector 11 which is photodiode. Alternatively, any other detector suitable for providing an electrical signal in dependence of the intensity of the weighed optical signal may be used. The detector is positioned at the same z-position as the grating but either above or below the grating, i.e. at a different y-position. This is a telecentric design.

Figure 5B:
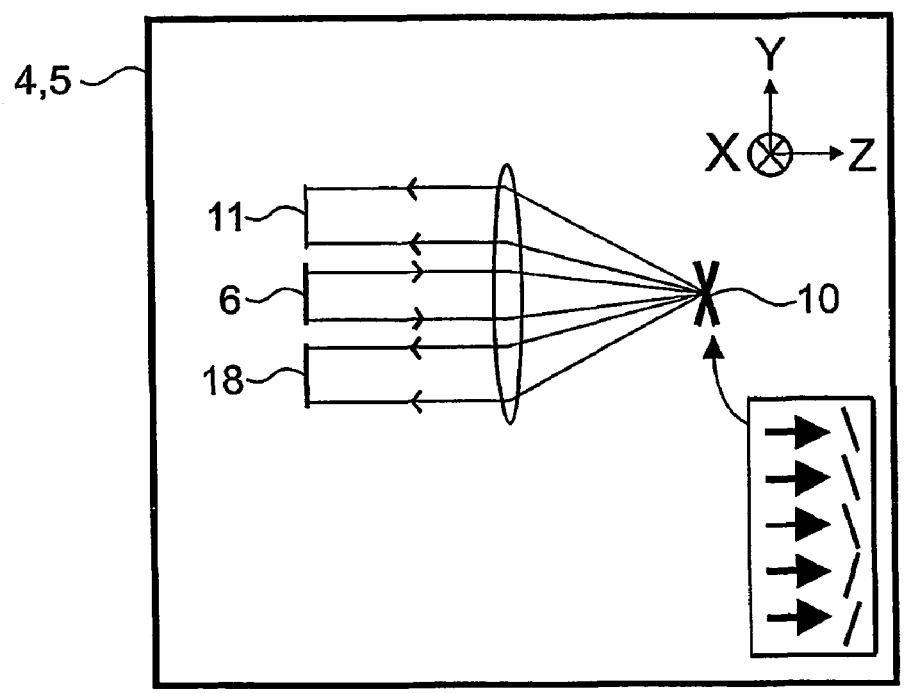

In the embodiment of FIG. 5B the MOE 10 is a DMD and substantially the entire surface is composed of tiltable reflective surfaces. Alternatively, a part of the surface or even the entire surface may be formed by reflective surfaces which are not tiltable but fixed. An example of this will be given below with reference to FIGS. 11A and 11B.

In the embodiment of FIGS. 4, 5A and 5B the MOE has two functions: it dumps those parts of the dispersed optical signal that should be measured by the other spectral filter, and it introduces the appropriate amplitude, i.e. gray scales for every wavelength for those parts of the dispersed optical signal that should be measured by this spectral filter. The amplitude adjustment may be done by fast repetitive tilting reflective surfaces between the signal path and the dump path, analogously to a DMD-based light valve as used e.g. in projection devices or displays.

A computational element 19 shown in FIG. 1 is arranged to calculate the difference between the positive and negative signal. This difference is proportional to the amplitude of the principal component of the optical signal. The amplitude of the principal component relates to the concentration of the substance, i.e. of the analyte. The relation between the amplitude and the concentration may be a linear dependence.

When the principal component comprises only a positive or only a negative component, only one spectral filter, one MOE and one detector may be used.

The embodiment of FIGS. 4, 5A and 5B has the advantage that it is relatively simple to align the beam path. In this embodiment part of the optical signal is lost in the spectral filters 4, 5 by first splitting the optical signal by the beam splitter 22. E.g. those parts of the optical signal which correspond to the positive part of the weighing function are dumped in the spectral filter that measures the optical signal weighed by the negative part of the weighing function. The same holds for the optical signal which correspond to the negative part of the weighing function and which is dumped in the spectral filter that measures the optical signal weighed by the positive part of the weighing function. In this embodiment two gratings 6 and two MOEs 10 are used. However, two separate optical paths using one and the same dispersive element 6 and/or one and the same MOE 10 are feasible as well, see e.g. FIGS. 8A and 8B.

Figure 6A:
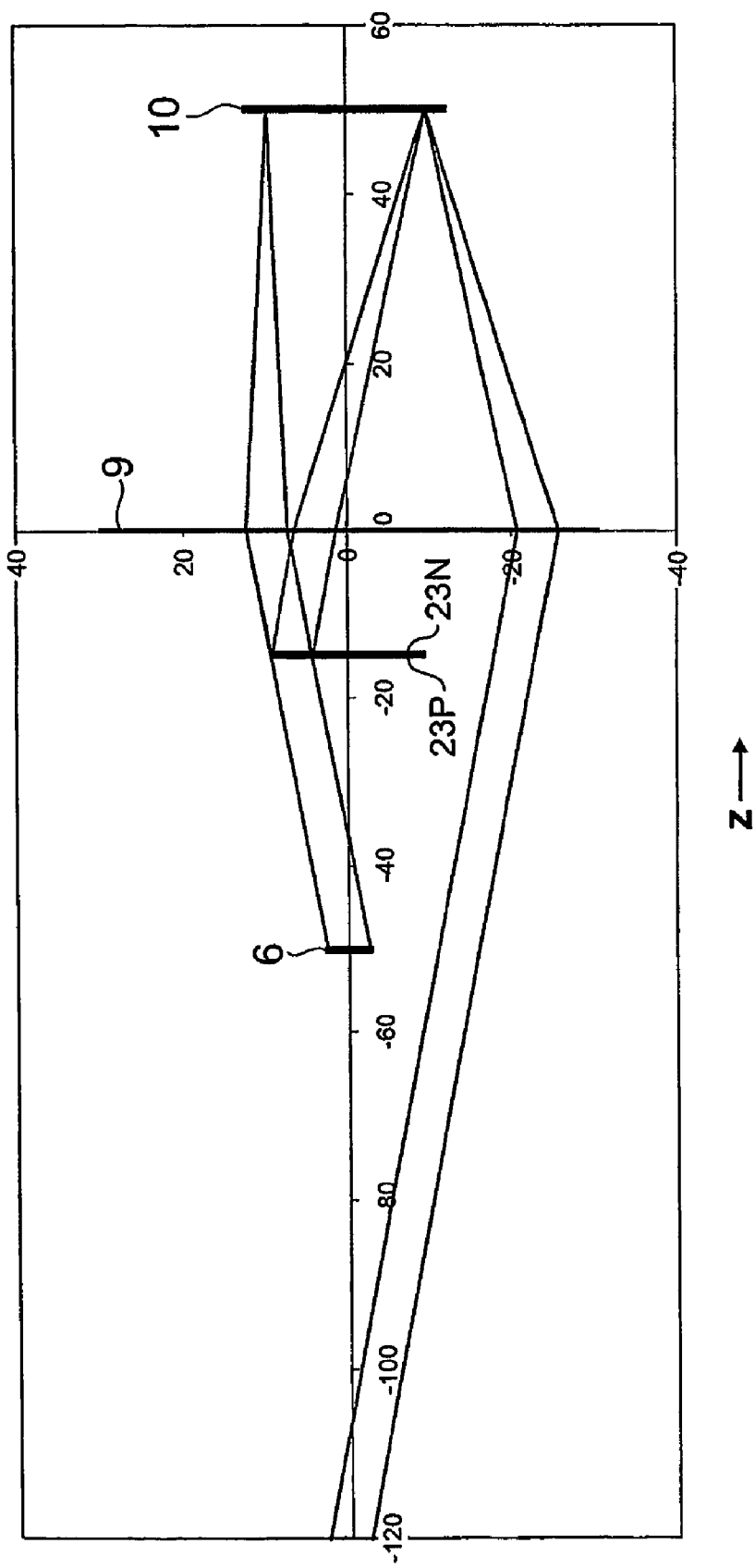
FIGS. 6A and 6B are schematic diagrams of another embodiment of the optical analysis system in the x-z plane and the y-z plane, respectively.
Figure 6B:
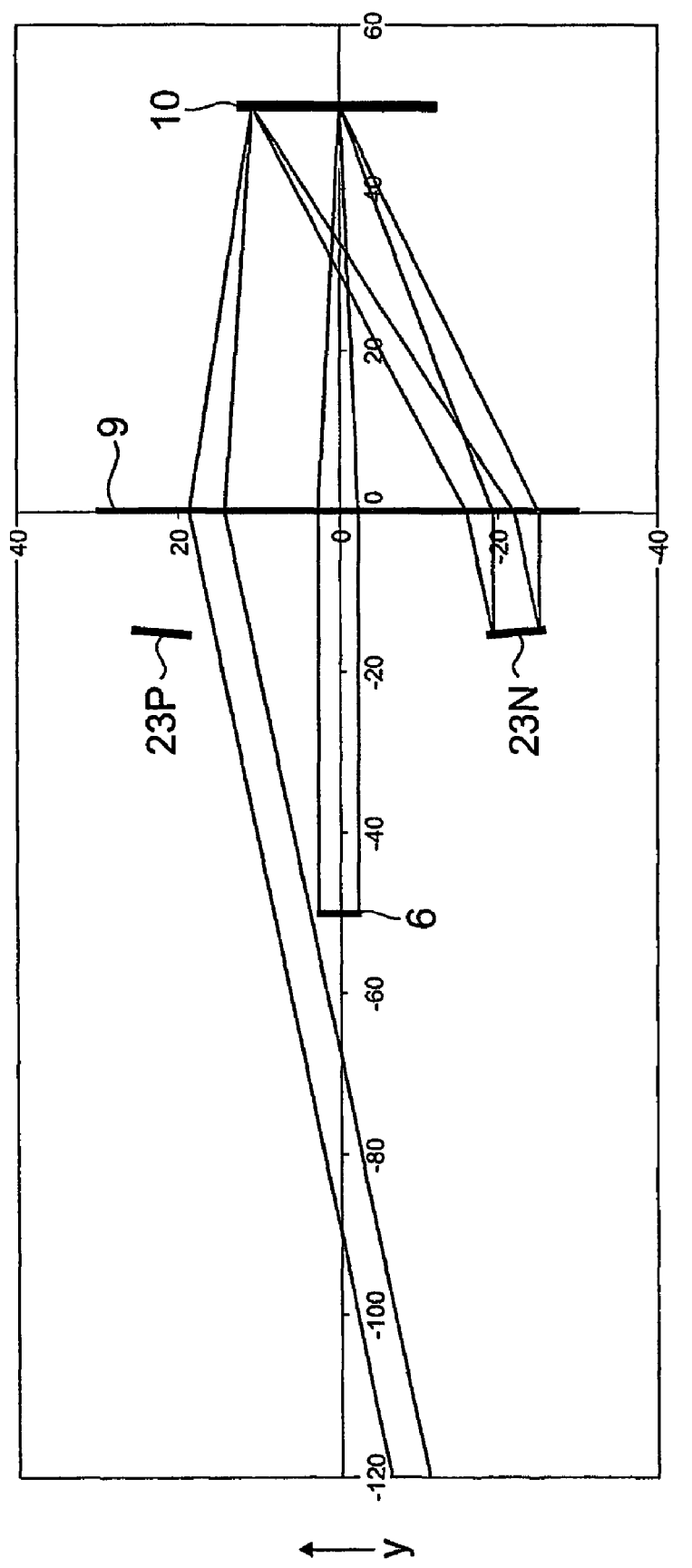

In the embodiment of the optical analysis system shown in FIGS. 6A and 6B the optical signal is not split by a beam splitter to separately spectrally filter the positive part and the negative part of the optical signal. Therefore, no optical signal is unnecessarily lost at the MOE and the optical signal is effectively used. Furthermore, only one grating and one MOE is used. The general idea is not to split the optical signal before it is incident on the dispersive element 6, but to do this afterwards, e.g. when the dispersed optical signal is incident on the MOE 10. Instead of dumping one of the two reflections off the MOE, both reflections are used and collected by a focusing member 9 analogously to FIGS. 5A and 5B. One of these reflections comprises the spectral components of the positive part P of the spectral weighing function, the other reflection comprises the spectral components of the negative part N of the spectral weighing function. Because the optical signal is first spectrally dispersed, the different spectral components are incident at different positions, in the example of FIGS. 6A and 6B at different x-positions, on the MOE 10. Therefore, the splitting into the positive part and the negative part may be done without loss of parts of the optical signal.

In the embodiment of FIG. 6A and 6B the optical signal has a beam diameter 5 mm. The beam is first spectrally dispersed by the dispersive element 6 which is a grating having for a particular wavelength a diffraction angle of 11 degrees off the optical axis, i.e. off the z-axis., in the dispersive x-z plane. In the non-dispersive y-z plane the beam position is not altered by the dispersive element. The optical signal incident on the grating comes from the sample 2 and propagates in the x-z plane. The dispersed optical signal is focused by the focusing member 9 onto the reflective MOE 10. In the example of FIGS. 6A and 6B the focusing member 9 is a lens having a focal distance of 50 mm. One ray is shown for one particular wavelength which is focused on one particular region of the MOE 10. Other wavelengths, not shown in FIGS. 6A and 6B are diffracted at a different angle off the dispersive element 6, but the corresponding rays, after the various reflections and refractions described below, all arrive at the same position, in this example at $(x,z)=(0,-120)$ mm. The other wavelengths, not shown in FIGS. 6A and 6B are focused on other regions of the MOE 10. Depending on whether a particular wavelength is comprised in the negative part N or the positive part P of the spectral weighing function the part of the MOE receiving this wavelength reflects it to one of the two folding mirrors 23P for the positive part P and 23N for the negative part N. On the path to the respective folding mirror 23P or 23N the corresponding ray is recollimated by focusing member 9. The folding mirrors 23P and 23N are positioned at $(y,z)=(+/-22$ mm, $-15$ mm) and rotated by 6 degrees in the y-z plane. The folding mirrors 23P and 23N direct the light incident thereon via the focusing member 9 to other regions of the MOE 10. In the example of FIGS. 6A and 6B these latter regions are at positive and negative y-values, respectively, whereas the region of the MOE 10 which reflects the optical signal the first time is at y=0. Instead of three different regions of one and the same MOE two or three different MOEs may be used. One, two or all of the MOBs, if two or three MOEs are used, may be operated in reflection or in transmission. In the example of FIGS. 6A and 6B a single DMD is used as a flexible, i.e. adjustable MOE. The DMD has tiltable elements with a reflective surface. The elements may be each tilted by deflection angles of plus or minus 12 degrees in y-z plane. In other words, the MOE is illuminated at three different regions: first central stripe close to y=0 and extending along the dispersive x-direction is illuminated for splitting positive and negative spectral parts. Subsequently, a stripe above this central stripe, i.e. at positive y-values and again extending along the dispersive x-direction is illuminated for introducing the required amplitude or grayscales for e.g. the positive part and a stripe below this central stripe, i.e. at negative y-values and again extending along the dispersive x-direction is illuminated for introducing the required amplitude or grayscales for e.g. the negative part.

This time, the MOE introduces the appropriate amplitude for each spectral component, i.e. it spectrally gray scales the optical signal according to the spectral weighing function, in a similar fashion as in the embodiment of FIGS. 4, 5A and 5B. For each spectral portion of the optical signal this adjustment of the amplitude is performed at a dedicated region of the MOE. All the light to be detected is captured by the focusing member 9 and directed towards two detectors, one detector 11P for the positive part and one detector 11N for the negative part. By placing detectors 11P and 11N at $(x,y,z)=(0,9,-120)$ and $(0,-9,-120)$ mm both the optical signal weighed by the first spectral weighing function and the optical signal weighed by the second spectral weighing function may be measured independently. The first spectral weighing function and the second spectral weighing function may correspond to the positive part P and the negative part N of the spectral weighing function shown e.g. in FIG. 3.

The optical analysis system 20 of FIGS. 6A and 6B is symmetric with respect to the x-z plane.

As shown in FIGS. 6A and 6B, the folding mirrors 23P and 23N are not positioned at the same y-position as the dispersive element 6. In this way the positive part and the negative part may be spatially separated thereby allowing for separate detection of these two parts. The parameters of FIGS. 6A and 6B are chosen such that light paths, for all colors and for both positive and negative part, can get around the folding mirrors 23P, 23N and the dispersive element 6 after the second reflection off the MOE 10. This design may require a focusing member with a sufficiently large capture angle in order not to loose any light. The resulting f-number of the focusing member 9 is approximately F#/1.0. The exact value may depend on the angles of the reflective surfaces and/or on the dispersive strength of the dispersive element 6.

Figure 7:
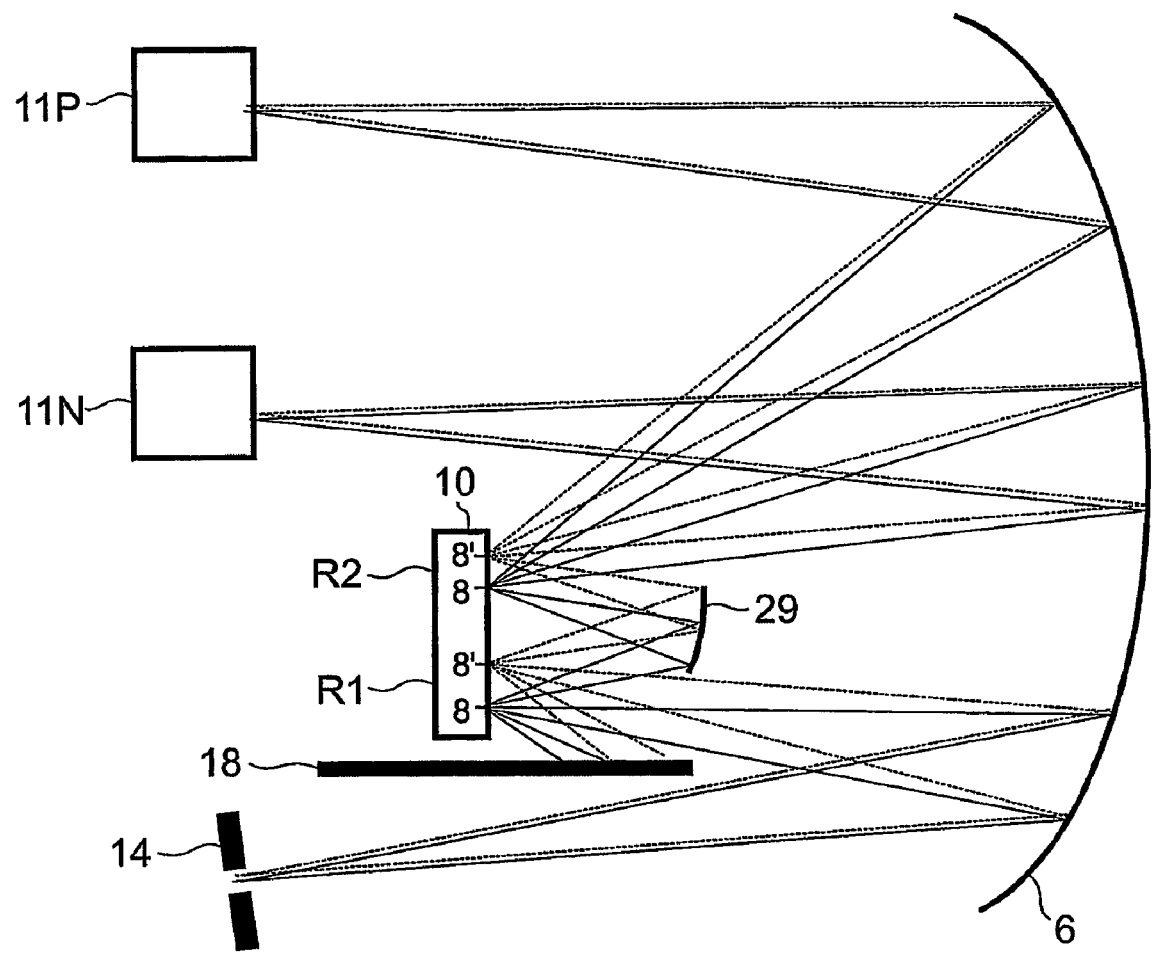
FIG. 7 is a schematic diagram of another embodiment of the optical analysis system.

In another embodiment shown in FIG. 7, the optical signal enters the optical analysis system 20 from a point source 14 which may be, e.g., a pin hole in a confocal detection scheme. From the point source 14 the diverging optical signal is directed to a dispersive element 6 which is a concave grating that images the dispersed optical signal on the MOE which may be a DMD. In a first step, the necessary gray scales are applied to the spectrum by switching the tiltable elements with an appropriate duty cycle. For each spectral portion the undesired fraction of the light is reflected towards a beam dump 18. The spectrum having the desired spectral intensities is reflected towards a further focusing member 29 which is a concave mirror. This mirror refocuses the spectrum to another part of the DMD. At the second reflection off the DMD, the spectrum is split into a first component and a second component which may correspond to the optical signal weighed by the positive part P and the negative part N of the spectral weighing function, respectively. The two components are then directed towards two detectors 11N, 11P. This may be achieved by a different part of the first concave grating, a separate grating, or one or more focusing members such as lenses or mirrors.

Alternatively or in addition, the fist component and the second component may correspond to a first principal component and a second spectral component, respectively. In the embodiment of FIG. 7 the dispersed optical signal is focused twice on regions of the MOE which are in one line oriented along the dispersive direction of the dispersive element 6. This simplifies the understanding of the principle. In a variation of this embodiment in which the MOE may be used more effectively, the two spectra are projected on the MOE as two parallel lines, i.e. one is above or below the plane of FIG. 7, the other spectrum may be in this plane.

Figure 8A:
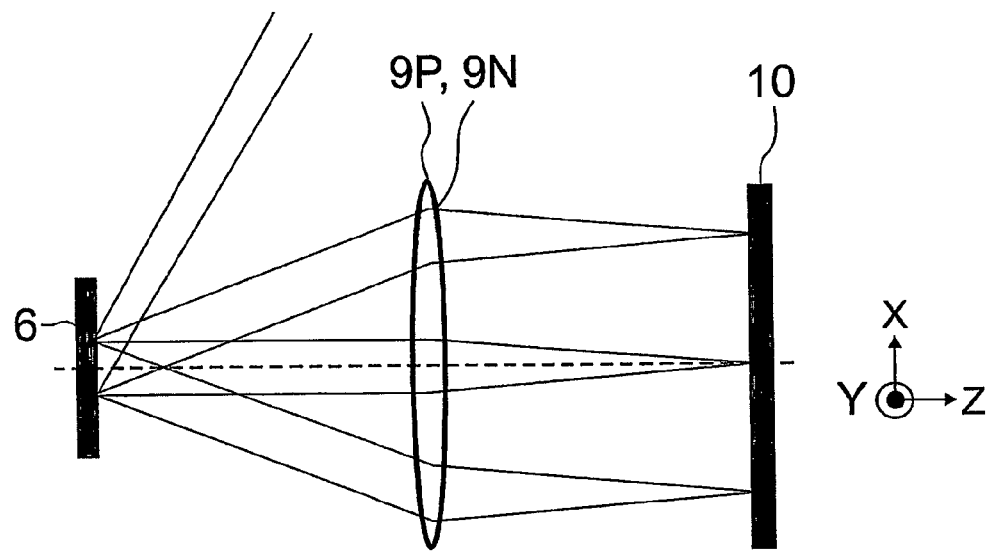
FIGS. 8A and 8B are schematic diagrams of another embodiment of the optical analysis system in the x-z plane and the y-z plane, respectively.
Figure 8B:
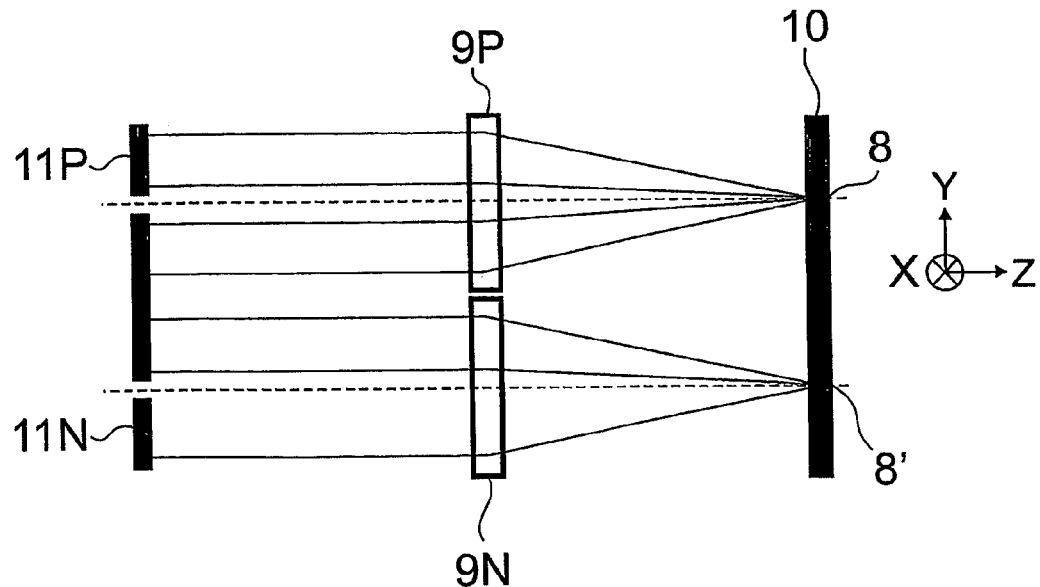

In the embodiment of FIGS. 8A and 8B the optical signal is spectrally dispersed by a diffractive element 6 which may be e.g. a grating or a prism. The reflective MOE may be a pixelated element such, e.g., an array of LC cells or of reflective electro-wetting cells. The incoming optical signal is first split into two beams of light by using e.g. a 50/50 beam splitter, not shown. The beam to be weighed by the positive part P of the spectral weighing function and the beam to be weighed by the negative part N of the spectral weighing function propagate parallel and are incident on a diffractive element 6 at different y-positions, but identical x- and z-positions. At the diffractive element light is spectrally dispersed, i.e. different spectral portions of the optical signal are diffracted by different angles. The dispersed optical signal is collected by two focusing members 9N, 9P such as e.g. lenses, one for each incident beam. The distances from the grating to the respective lens 9N, 9P and from the respective lens 9N, 9P to the MOE 10 are equal and correspond to the focal distance of the lens (telecentric design). The result is that converging pencils of light are normal incident at the MOE 10 in the x-z plane, for all spectral portions. Different x-positions at the reflective MOE 10 receive different spectral portions indicated for two particular wavelengths by reference numerals 8 and 8'. The MOE 10 is arranged to reflect the incident dispersed optical signal with a reflection coefficient which varies as function of the x-position. This introduces the appropriate gray-scales that construct the spectral weighing function.

After reflection off the MOE 10, the light is collected by the focusing members 9P, 9N and directed towards two detectors, one detector 11P for detecting the optical signal weighed by the first spectral weighing function corresponding to the positive part P of the spectral weighing function, and one detector 11N for detecting the optical signal weighed by the second spectral weighing function corresponding to the negative part N of the spectral weighing function. The optical axes of the two lenses 9P, 9N are parallel but displaced in the y-direction so that the light reflected off MOE 10 can be spatially separated from the diffractive element 6.

Figure 9A:
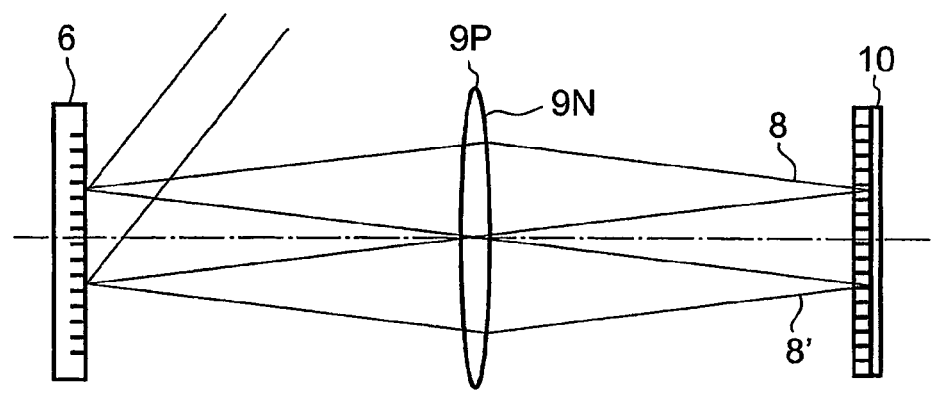
FIGS. 9A and 9B are schematic diagrams of yet another embodiment of the optical analysis system in the x-z plane and the y-z plane, respectively.
Figure 9B:
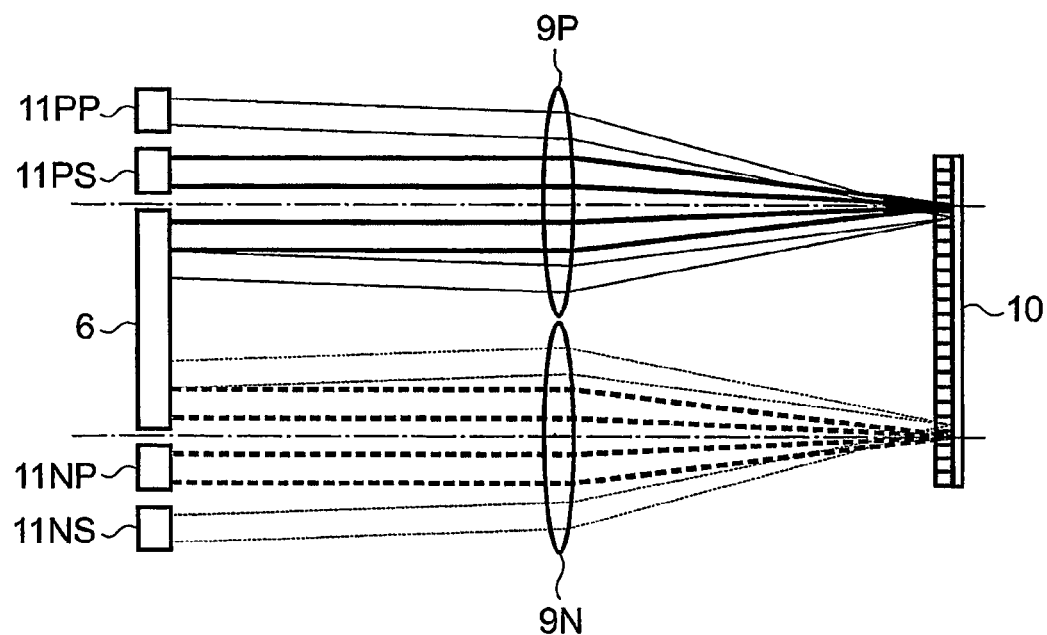

When the reflectivity of the MOE 10 is polarization dependent as is the case e.g. for a MOE comprising a reflective LC cell, the MOE 10 ma often have a limited efficiency because it only works for light with one specific polarization. In the embodiment shown in FIGS. 9A and 9B an efficient optical analysis system 20 comprising an MOE 10 with an array of reflective LC cells is used. Before entering the spectrometer the optical signal is split into four beams, two with a s-polarization and two with a p-polarization. Then the beams with p-polarization are converted to s-polarization, e.g. by a half lambda plate or by a sequence of tilted mirrors. These four beams are incident on the dispersing element 6.

In this embodiment the MOE 10 is an array of reflective LC cells which each comprise three elements: a sheet polarizer transmitting s-polarized light, layer of LC molecules, and a reflective surface. Depending on the orientation of the LC molecules induced by the voltage applied to the respective LC cell part of the light reflected by the reflective surface is absorbed by the polarizer. In this way the spectrally dispersed optical signal is weighed.

The incoming optical signal is first split into two beams of light by using e.g. a regular 50/50 beam splitter, not shown. One of these two beams shown by the solid lines is weighed by the first spectral weighing function corresponding to the positive part P of the spectral weighing function the other of these two beams shown by the dashed lines is weighed by the second spectral weighing function corresponding to the negative part N of the spectral weighing function. These two beams propagate parallel.

Each of these beams is split into two beams having different polarizations, e.g. one being s-polarized, the other being p-polarized. One beam shown by a thick line has a polarization direction that is transmitted by the sheet polarizer, i.e. in this example s-polarization. The polarization of this beam is not changed prior to the dispersive element 6. The other beam shown by a thin line has a polarization direction that is absorbed by the sheet polarizer, i.e. in this example p-polarization. The polarization of this beam is rotated by 90 degrees prior to the dispersive element 6, for instance by a half lambda plate. The beams whose polarization has been changed are not parallel in the y-direction to the beams whose polarization remained unchanged.

The four resulting beams are incident on a diffractive element 6, which is a grating, at different y-positions, but identical x- and z-positions. At the diffractive element 6 light is spectrally dispersed. The spectrally dispersed light is collected by two focusing members, one focusing member 9P for the optical signal to weighed by the first spectral weighing function which may correspond to the positive part P of the spectral weighing function, and one focusing member 9N for the optical signal to weighed by the second spectral weighing function which may correspond to the negative part N of the spectral weighing function. The distances from the grating to the respective lens and from the respective lens to the MOE are both equal and correspond to the focal distance of the respective lens (telecentric design).

The result is that the converging pencils of light towards the MOE 10 are normal incident on the MOE 10 in the x-z plane, for all spectral portions of the optical signal. Different x-positions at the MOE 10 receive different spectral portions. The MOE 10 which is a reflective pixelated element is arranged to reflect the incident dispersed optical signal with a reflection coefficient which varies as function of the x-position thereby introducing the required spectral weighing according to the spectral weighing function. After reflection off the MOE 10, the light is collected by the focusing members 9P, 9N again and directed towards four detectors, one detector 11PP for detecting the p-polarized part of the optical signal weighed by the first spectral weighing function which may correspond to the positive part P of the spectral weighing function, one detector 11PS for detecting the s-polarized part of the optical signal weighed by the first spectral weighing function which may correspond to the positive part P of the spectral weighing function, one detector 11NP for detecting the p-polarized part of the optical signal weighed by the second spectral weighing function which may correspond to the negative part N of the spectral weighing function, and one detector 11NS for detecting the s-polarized part of the optical signal weighed by the second spectral weighing function which may correspond to the negative part N of the spectral weighing function.

The optical axes of the two focusing members 9P and 9N are parallel but displaced in the y-direction so that the reflected light off the MOE 10 can be spatially separated from the diffractive element 6.

Figure 10A:
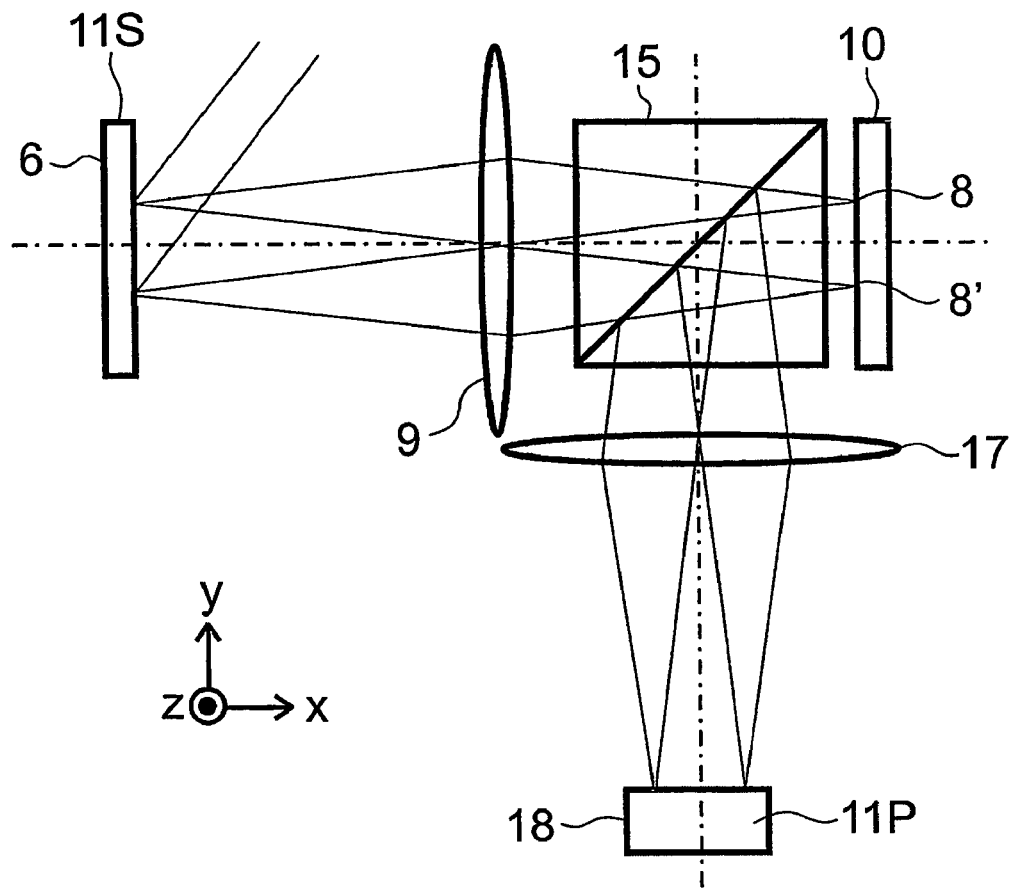
FIGS. 10A, 10B and 10C are schematic diagrams of yet another embodiment of the optical analysis system in the x-y plane, the y-z plane and the x-z plane, respectively.
Figure 10B:
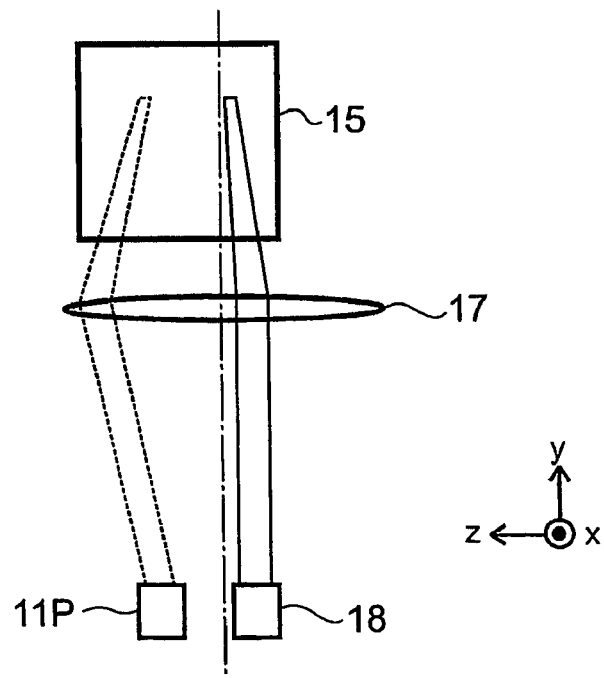
Figure 10C:
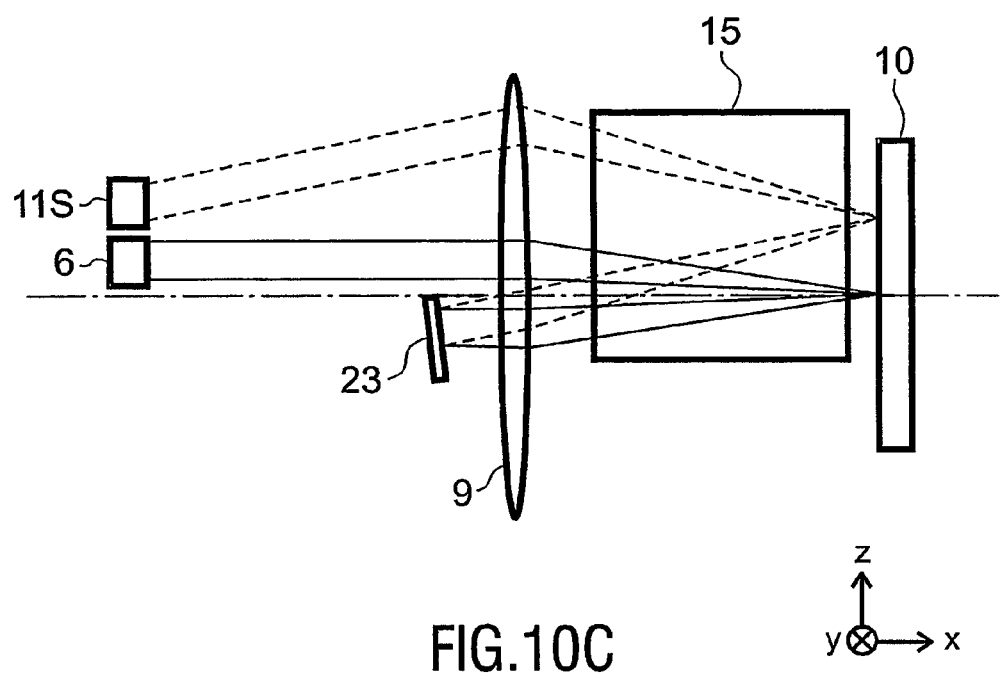

In another embodiment shown in FIGS. 10A, 10B and 10C the MOE 10 comprises an array of LC cells. In contrast to the embodiments described above with reference to FIGS. 4, 5A, 5B, 8A, 8B, 9A and 9B the incoming optical signal is not split into two beams for the positive and negative part prior to the dispersive element 6 in this embodiment. The LC cell used in this embodiment is similar to that described above with reference to FIGS. 9A and 9B but does not contain a polarizer. The result is that substantially all, except for unwanted loss in the layer of the LC molecules, incident light is reflected, however the polarization direction of the light may be changed due to the anisotropic index of refraction which may be adjusted by application of a voltage across the LC cell. In FIG. 10A only one incoming beam with only s-polarized light is shown. The incoming light may be unpolarized or partially polarized having e.g. linear or circular polarization. In these cases the incoming beam may be decomposed into two beams having s-polarization and p-polarization analogously to the embodiment described with reference to FIGS. 9A and 9B. For reasons of clarity only a single beam is drawn in FIGS. 10A, 10B and 10C.

In FIG. 10A the incoming light is the part of the optical signal having s-polarization, which is parallel to the z-axis direction. The incoming light is incident on a dispersive element 6 where the optical signal is spectrally dispersed, i.e. the different spectral portions are dispersed over different angles. The dispersed optical signal is at least partly collected by a focusing member 9, which is a lens, and focused on a MOE 10 which is an array of reflective LC cells. The distances from the grating to the lens and from the lens to the LC cell are equal and correspond to the focal distance of the lens (telecentric design). The result is that converging pencils of light propagating towards the MOE 10 are normal incident on the MOE 10 in the x-z plane, for all spectral portions of the optical signal. Different x-positions of the MOE 10 correspond to different spectral portions of the optical signal.

Between the focusing member 9 and the MOE 10 a polarizing beam splitter (PBS) 15 is positioned. The incoming s-polarized light is transmitted by PBS 15. The array of LC cells contains no polarization filter and, therefore, reflects substantially all the light incident thereon. The polarization direction of the light is changed by an amount depending on the voltages across the LC cells. The amount of polarization rotation is determined by the absolute value of the spectral weighing function in the respective spectral range. The light reflected from the LC cell is directed to the PBS 15. The p-component of the light incident on the PBS 15 is reflected by the PBS 15 and focused by a further focusing member 17 on a beam dump 18. The s-component of the light incident on the PBS 15 is transmitted by PBS 15 and incident on a folding mirror 23. The distance from folding mirror 23 to the lens is not equal to the focal length of the lens. The light reflected by folding mirror 23 is focused by the focusing member 9 on the MOE 10. Because the folding mirror 23 is at a slight angle with respect to direction of the incident light, the light reflected by the folding mirror 23 reaches the MOE 10 at a different z-position. Also the x-position of the light on the LC-cell (6) is reflected with respect to the optical axis compared to the x-position of the first reflection.

For light with a wavelength corresponding to positive values of the regression vector the polarization is not changed by the LC cell. This s-polarized light is transmitted for the fourth time by the PBS and focused by lens (4) on detector (3). For light with a wavelength corresponding to negative values of the regression vector the polarization is rotated by 90 degrees by the LC cell. This p-polarized light reflected by the PBS and focused by lens (7) on detector (9).

In this embodiment the LC cell does not contain a polarizer. Therefore, all light is reflected and only the polarization direction of the light may be changed.

The incident light is not on the optical axis of the focusing member 9, therefore the incoming and returned light do not overlap and it is possible to use the folding mirror 23. Preferably the incoming light incident on the focusing member is off-axis from the optical axis of the focusing member 9 and substantially perpendicular to the dispersion direction of the dispersive element 6 to allow for a relatively small lens diameter.

The distance from dispersive element 6 to the focusing member 9 and the distance from the focusing member 9 to the MOE 10 may be both equal to the focal length of the focusing member 9 (telecentric design). The result is that the converging pencils of light are normal incident on the MOE 10 in the x-z plane, for all spectral components.

The distance from the focusing member 9 to the detector 11S may be equal to the focal length of the focusing member 9. In this case the detector 11S may have a relatively small area.

The distance from the MOE 10 to the focusing member 17 and the distance the focusing member 17 to beam dump 18 and/or to the detector 11P may be each equal to the focal length of the focusing member 9 (telecentric design).

The distance from folding mirror 23 to the main plane of the focusing member 9 may be different from the focal length of focusing member 9 (non-telecentric design). In this way the detector 11S may have a different position than the dispersive element 6.

Figure 11A:
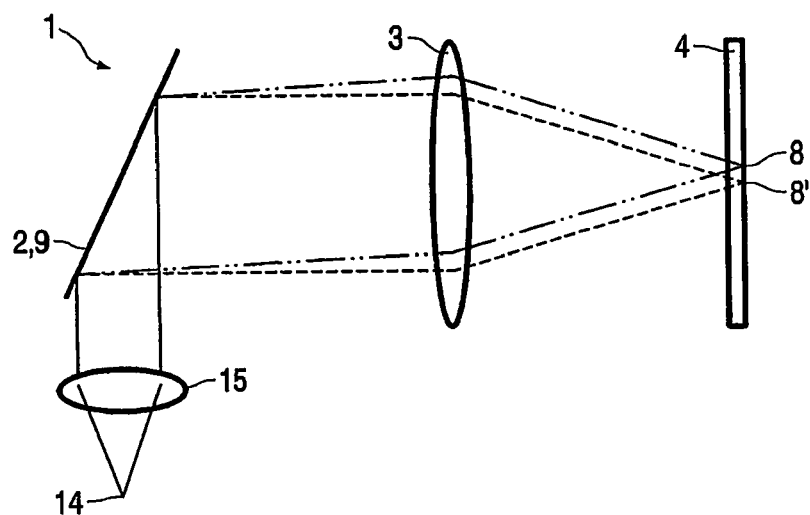
FIGS. 11A and 11B are schematic diagrams of yet another embodiment of the optical analysis system in the x-z plane and the y-z plane, respectively.
Figure 11B:
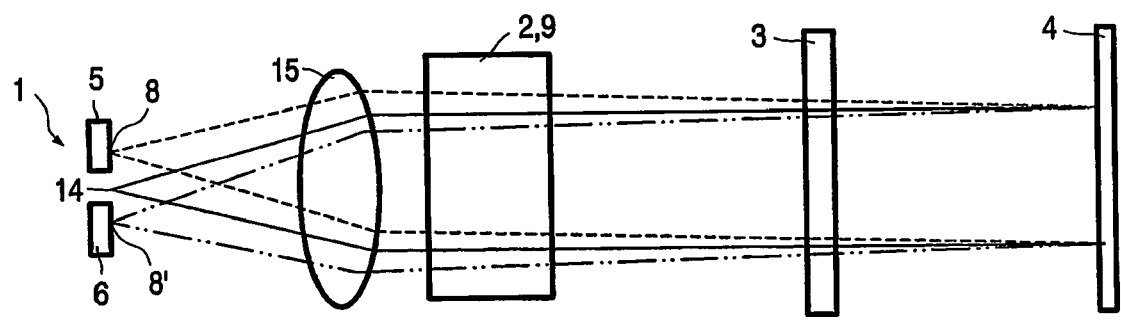
Figure 12:
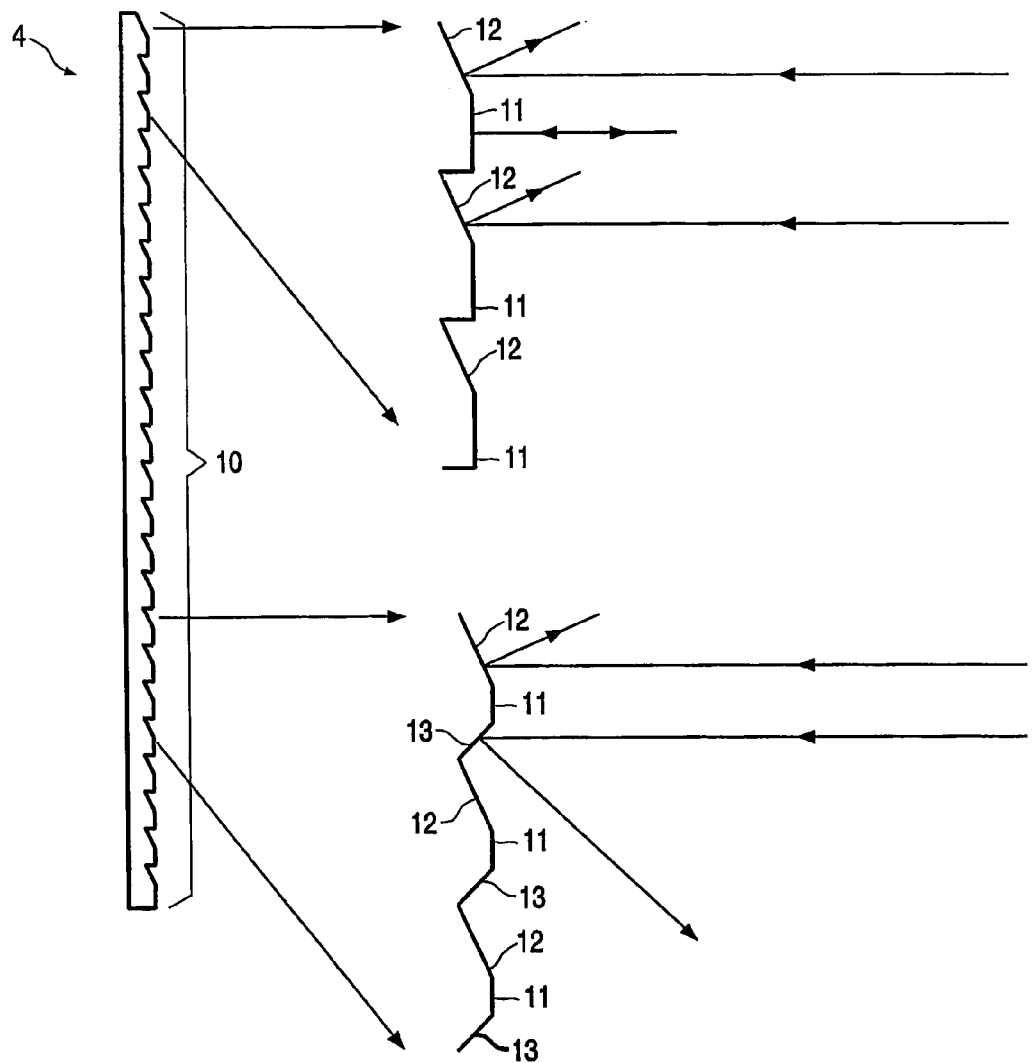
FIG. 12 is a cross sections of an embodiment of the distribution element.

In the embodiment shown in FIGS. 11A and 11B, the optical analysis system 1 comprises a further dispersive element 9 for spectrally recombining the first part of the optical signal prior to focusing the first part on the first detector 5. In this embodiment the optical signal enters the optical analysis system 1 from a point source 14 which may be, e.g., a pin hole in a confocal detection scheme. The optical analysis system 1 comprises a lens 15 for collimating the optical signal, and a dispersive element 2, which is a grating, and a focusing member 3, which is a cylinder lens. Focusing member 3 is arranged to focus the dispersed optical signal on distribution element 4. In this embodiment distribution element 4 shown in FIG. 12 is arranged to reflect the dispersed optical signal back towards the focusing member 3 for re-collimation. The re-collimated optical signal is then still spectrally dispersed which limits the possibility to focus it to a relatively small spot size. To spatially recombine the optical signal it is sent to the further dispersive element 9 which in this embodiment is the dispersive element 3, i.e. the dispersive element 3 and the further dispersive element 9 are integrated in one grating. The spectrally recombined optical signal weighted by the first spectral weighing function and the spectrally recombined optical signal weighted by the second spectral weighing function are focused on the first detector 5 and the second detector 6 by lens 15.

Note that the optical designs presented in the embodiments are not the only possible design. Besides trivial variations of parameters, other schemes, especially with respect to reflections in different directions and different detector positions are conceivable.

The invention claimed is:

1. An optical analysis system for determining an amplitude of a principal component of an optical signal, the optical analysis system comprising:
   a multivariate optical element with at least one electro-wetting cell for reflecting the optical signal and thereby weighing the optical signal by a spectral weighing function, and
   a detector for detecting the weighed optical signal.

2. An optical analysis system as claimed in claim 1, further comprising a dispersive element for spectrally dispersing the optical signal, the multivariate optical element being arranged to receive the dispersed optical signal.

3. An optical analysis system as claimed in claim 2, wherein the multivariate optical element comprises a region for receiving a spectral portion of the dispersed optical signal, the region having a reflectivity relating to the spectral weighing function.

4. An optical analysis system as claimed in claim 2, wherein the multivariate optical element comprises a region for receiving a spectral portion of the dispersed optical signal, a part of the region being arranged to reflect the dispersed optical signal incident thereon to the detector, another part of the region being arranged to prevent the dispersed optical signal incident thereon from being reflected to the detector.

5. An optical analysis system as claimed in claim 3, wherein the at least one electro-wetting cell is in the region for receiving a spectral portion of the dispersed optical signal.

6. An optical analysis system as claimed in claim 2, wherein the detector comprises a first detector for detecting th& optical signal weighted by a first spectral weighing function and a second detector for detecting the optical signal weighted by a second spectral weighing function, the multivariate optical element being arranged to reflect a first part of the dispersed optical signal weighted by the first spectral weighing function to the first detector and a second part of the optical signal weighted by the second spectral weighing function to the second detector.

7. An optical analysis system as claimed in claim 1, wherein the multivariate optical element comprises a first multivariate optical element weighing the optical signal by a first partial weighing function and a second multivariate optical element for weighing the optical signal weighed by the first partial weighing function by a second partial weighing function.

8. An optical analysis system as claimed in claim 1, further comprising a light source for providing light for illuminating a sample comprising a substance having a concentration and thereby generating the principal component, the amplitude of the principal component relating to the concentration of the substance.

9. A blood analysis system comprising an optical analysis system as claimed in claim 8, the sample comprising blood.

10. A method of determining an amplitude of a principal component of an optical signal, the method comprising the steps of
    reflecting the optical signal by a multivariate optical element having a spectral reflectivity corresponding to a spectral weighing function, and
    detecting the optical signal reflected by the multivariate optical element,
    wherein the multivariate optical element comprises a region for receiving a spectral portion of the dispersed optical signal, the region having a reflectivity relating to the spectral weighing function and at least one reflective electro-wetting cell.

11. An optical analysis system for determining an amplitude of a principal component of an optical signal, the optical analysis system comprising:
    a multivariate optical element for reflecting the optical signal and thereby weighing the optical signal by a spectral weighing function, wherein the multivariate optical element comprises a region for receiving a spectral portion of the dispersed optical signal, the region having a reflectivity relating to the spectral weighing function,
    a dispersive element for spectrally dispersing the optical signal, the multivariate optical element being arranged to receive the dispersed optical signal, and
    a detector for detecting the weighed optical signal,
    wherein the region comprises a reflective electro-wetting cell.

12. An optical analysis system as claimed in claim 11, wherein a first part of the region is arranged to reflect the dispersed optical signal incident thereon to the detector, and a second part of the region being arranged to prevent the dispersed optical signal incident thereon from being reflected to the detector.

13. An optical analysis system as claimed in claim 11, wherein the detector comprises a first detector for detecting the optical signal weighted by a first spectral weighing function and a second detector for detecting the optical signal weighted by a second spectral weighing function, the multivariate optical element being arranged to reflect a first part of the dispersed optical signal weighted by the first spectral weighing function to the first detector and a second part of the optical signal weighted by the second spectral weighing function to the second detector.

14. An optical analysis system as claimed in claim 11, wherein the multivariate optical element comprises a first multivariate optical element weighing the optical signal by a first partial weighing function and a second multivariate optical element for weighing the optical signal weighed by the first partial weighing function by a second partial weighing function.

15. An optical analysis system as claimed in claim 11, further comprising a light source for providing light for illuminating a sample comprising a substance having a concentration and thereby generating the principal component, the amplitude of the principal component relating to the concentration of the substance.

16. A blood analysis system comprising an optical analysis system as claimed in claim 15, the sample comprising blood.

* * * * *